United States Patent
Ban et al.

(10) Patent No.: US 9,904,455 B2
(45) Date of Patent: Feb. 27, 2018

(54) METHOD AND APPARATUS FOR CHANGING USER INTERFACE BASED ON USER MOTION INFORMATION

(71) Applicant: Samsung Electronics Co., Ltd., Suwon-si, Gyeonggi-do (KR)

(72) Inventors: Dae-hyun Ban, Seoul (KR); Su-jin Kim, Yongin-si (KR); Jeong-ho Han, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 546 days.

(21) Appl. No.: 14/320,924

(22) Filed: Jul. 1, 2014

(65) Prior Publication Data

US 2015/0089411 A1    Mar. 26, 2015

(30) Foreign Application Priority Data

Jul. 1, 2013 (KR) .................. 10-2013-0076586

(51) Int. Cl.
| | |
|---|---|
| G06F 3/0486 | (2013.01) |
| A61B 8/00 | (2006.01) |
| G06F 3/01 | (2006.01) |
| G06F 3/0484 | (2013.01) |
| G06F 3/03 | (2006.01) |
| G06F 19/00 | (2018.01) |

(Continued)

(52) U.S. Cl.
CPC .............. *G06F 3/0486* (2013.01); *A61B 8/44* (2013.01); *A61B 8/4477* (2013.01); *A61B 8/467* (2013.01); *G06F 3/011* (2013.01); *G06F 3/0304* (2013.01); *G06F 3/03549* (2013.01); *G06F 3/0481* (2013.01); *G06F 3/0488* (2013.01); *G06F 3/04842* (2013.01); *G06F 3/04845* (2013.01); *G06F 19/3406* (2013.01); *A61B 8/4405* (2013.01); *A61B 8/4427* (2013.01); *A61B 8/465* (2013.01); *G01S 7/52084* (2013.01)

(58) Field of Classification Search
CPC .... G06F 3/011; G06F 3/0304; G06F 3/03549; G06F 3/0481
USPC ........................................................ 715/765
See application file for complete search history.

(56) References Cited

U.S. PATENT DOCUMENTS

| | | | |
|---|---|---|---|
| 5,715,823 A | 2/1998 | Wood et al. | |
| 6,072,463 A * | 6/2000 | Glaser ..................... G06F 3/038 379/262 |

(Continued)

FOREIGN PATENT DOCUMENTS

| | | |
|---|---|---|
| CN | 1716171 A | 1/2006 |
| CN | 101098424 A | 1/2008 |

(Continued)

OTHER PUBLICATIONS

Office Action dated Feb. 4, 2016 in related U.S. Appl. No. 14/755,486.

(Continued)

*Primary Examiner* — David Phantana-angkool
(74) *Attorney, Agent, or Firm* — Staas & Halsey LLP

(57) ABSTRACT

A method of changing a user interface (UI), which is used for diagnosis of a target object via a medical device, based on user motion information. The method including obtaining motion information regarding a user; changing the UI based on the obtained motion information regarding the user; and displaying the changed UI.

26 Claims, 19 Drawing Sheets

(51) Int. Cl.
    *G06F 3/0354* (2013.01)
    *G06F 3/0488* (2013.01)
    *G06F 3/0481* (2013.01)
    *G01S 7/52* (2006.01)

(56) References Cited

U.S. PATENT DOCUMENTS

| | | | |
|---|---|---|---|
| 7,549,961 B1* | 6/2009 | Hwang | A61B 8/14 600/301 |
| 7,904,824 B2 | 3/2011 | Stern et al. | |
| 8,069,420 B2* | 11/2011 | Plummer | G06F 19/321 600/921 |
| 8,085,244 B2 | 12/2011 | Shows | |
| 8,272,387 B2 | 9/2012 | Essex et al. | |
| 8,784,314 B2 | 7/2014 | Mathew | |
| 9,021,358 B2* | 4/2015 | Amble | G06Q 50/24 600/301 |
| 9,165,112 B2 | 10/2015 | Doyle | |
| 9,256,342 B2* | 2/2016 | Davidson | G06F 3/0481 |
| 9,384,014 B2* | 7/2016 | Kim | G06F 9/4445 |
| 9,433,339 B2* | 9/2016 | Allyn | A61B 1/0676 |
| 9,465,437 B2* | 10/2016 | Kim | G06F 3/0485 |
| 9,489,114 B2* | 11/2016 | Coplen | G06F 3/04847 |
| 9,517,184 B2* | 12/2016 | Branconier | A61J 15/0026 |
| 9,531,699 B2* | 12/2016 | Panchura | H04L 63/08 |
| 9,552,671 B2* | 1/2017 | Park | G06F 3/04815 |
| 9,591,224 B2* | 3/2017 | Jung | H04N 5/23293 |
| 2004/0242988 A1 | 12/2004 | Niwa et al. | |
| 2005/0080326 A1 | 4/2005 | Mathew | |
| 2005/0131856 A1 | 6/2005 | O'Dea | |
| 2006/0020206 A1 | 1/2006 | Serra et al. | |
| 2006/0050142 A1 | 3/2006 | Scott et al. | |
| 2006/0058654 A1 | 3/2006 | Di Marco | |
| 2006/0068834 A1 | 3/2006 | Jones | |
| 2008/0072151 A1 | 3/2008 | Song et al. | |
| 2008/0079696 A1 | 4/2008 | Shim et al. | |
| 2008/0119731 A1 | 5/2008 | Becerra et al. | |
| 2008/0125655 A1 | 5/2008 | Song et al. | |
| 2009/0012394 A1 | 1/2009 | Hobelsberger | |
| 2009/0024787 A1 | 1/2009 | Yim | |
| 2009/0027347 A1 | 1/2009 | Wakefield et al. | |
| 2009/0043195 A1 | 2/2009 | Poland | |
| 2009/0131793 A1 | 5/2009 | Stonefield et al. | |
| 2009/0156934 A1 | 6/2009 | Lee et al. | |
| 2009/0164896 A1 | 6/2009 | Thorn | |
| 2009/0247874 A1 | 10/2009 | Kim | |
| 2010/0049050 A1 | 2/2010 | Pelissier | |
| 2010/0049051 A1 | 2/2010 | Sang et al. | |
| 2010/0094132 A1 | 4/2010 | Hansen et al. | |
| 2010/0145195 A1 | 6/2010 | Hyun | |
| 2010/0156865 A1 | 6/2010 | Kreek et al. | |
| 2010/0180219 A1 | 7/2010 | Sung et al. | |
| 2010/0191120 A1 | 7/2010 | Kraus et al. | |
| 2010/0293508 A1* | 11/2010 | Hwang | G06F 3/04886 715/846 |
| 2010/0325546 A1* | 12/2010 | Leo | G06F 19/3406 715/719 |
| 2011/0190034 A1 | 8/2011 | Shin | |
| 2012/0069010 A1 | 3/2012 | Tian et al. | |
| 2012/0139845 A1 | 6/2012 | Griffin | |
| 2012/0145783 A1 | 6/2012 | Landau | |
| 2012/0172726 A1* | 7/2012 | Sakai | A61B 8/00 600/443 |
| 2012/0179039 A1* | 7/2012 | Pelissier | A61B 8/4263 600/443 |
| 2012/0290976 A1* | 11/2012 | Lahm | G06F 19/3406 715/810 |
| 2012/0293431 A1 | 11/2012 | Hauf | |
| 2013/0018263 A1 | 1/2013 | Kimoto | |
| 2013/0035139 A1 | 2/2013 | Sheynblat et al. | |
| 2013/0137987 A1 | 5/2013 | Abe et al. | |
| 2013/0158397 A1 | 6/2013 | K. | |
| 2013/0165784 A1 | 6/2013 | Kim | |
| 2013/0194891 A1 | 8/2013 | Kristoffersen et al. | |
| 2013/0219317 A1 | 8/2013 | Jo et al. | |
| 2013/0225999 A1 | 8/2013 | Banjanin | |
| 2013/0281855 A1 | 10/2013 | Baba et al. | |
| 2013/0335441 A1* | 12/2013 | Zalev | A61B 5/7203 345/629 |
| 2014/0005550 A1 | 1/2014 | Lu et al. | |
| 2014/0063219 A1 | 3/2014 | Stonefield | |
| 2014/0221835 A1 | 8/2014 | Ota | |
| 2014/0282142 A1* | 9/2014 | Lin | A61B 8/467 715/765 |
| 2014/0378833 A1 | 12/2014 | Cheng | |
| 2015/0002490 A1 | 1/2015 | Han et al. | |
| 2016/0062470 A1* | 3/2016 | Pandey | G06F 3/017 345/156 |
| 2016/0267755 A1* | 9/2016 | Martinson | G08B 6/00 |
| 2016/0313820 A1* | 10/2016 | Ancona | G06F 3/044 |
| 2016/0313821 A1* | 10/2016 | Bui | G06F 1/1632 |
| 2016/0313822 A1* | 10/2016 | Krishnakumar | G06F 1/1632 |
| 2017/0105701 A1* | 4/2017 | Pelissier | A61B 8/4254 |
| 2017/0123487 A1* | 5/2017 | Hazra | G06F 3/015 |
| 2017/0157431 A1* | 6/2017 | Cheatham, III | A61N 7/00 |
| 2017/0164876 A1* | 6/2017 | Hyde | A61B 5/1118 |
| 2017/0172545 A1* | 6/2017 | Lee | A61B 8/463 |
| 2017/0173262 A1* | 6/2017 | Veltz | A61M 5/1723 |
| 2017/0179774 A1* | 6/2017 | Jin | H02J 50/90 |

FOREIGN PATENT DOCUMENTS

| | | |
|---|---|---|
| CN | 101595648 A | 12/2009 |
| CN | 101828380 A | 9/2010 |
| EP | 1 780 991 A1 | 5/2007 |
| EP | 1 925 257 A1 | 5/2008 |
| EP | 2458472 A1 | 5/2012 |
| JP | 2005-144154 | 6/2005 |
| JP | 2005-270317 | 10/2005 |
| JP | 2007-97816 | 4/2007 |
| JP | 2009-148 | 1/2009 |
| KR | 10-2009-0050423 | 5/2009 |
| KR | 10-2009-0076994 | 7/2009 |
| KR | 10-2010-0084037 | 7/2010 |
| KR | 10-2011-0136098 | 12/2011 |
| WO | 2011/159034 A2 | 12/2011 |

OTHER PUBLICATIONS

Korean Office Action dated Sep. 30, 2015 in corresponding Korean Patent Application No. 10-2013-0076586.
Korean Office Action dated Nov. 30, 2015 in corresponding Korean Patent Application No. 10-2013-0076586.
Office Action dated Jul. 8, 2015 in related U.S. Appl. No. 14/685,998.
U.S. Appl. No. 14/685,998, filed Apr. 14, 2015, Dae-hyun Ban, Samsung Electronics Co., Ltd.
U.S. Appl. No. 14/755,486, filed Jun. 30, 2015, Dae-hyun Ban, Samsung Electronics Co., Ltd.
Office Action dated Nov. 30, 2015 in related U.S. Appl. No. 14/685,998.
Korean Office Action dated Jun. 12, 2015 in corresponding Korean Patent Application No. 10-2015-0066249.
Extended European Search Report dated Aug. 11, 2015 in corresponding European Patent Application No. 15163020.9.
European Office Action dated Aug. 18, 2015 in corresponding European Patent Application No. 14 174 629.7.
Korean Office Action dated Nov. 27, 2014 in corresponding Korean Patent Application No. 10-2013-0076586.
Extended European Search Report dated Oct. 30, 2014 in corresponding European Patent Application No. 14174629.7.
European Office Action dated Mar. 21, 2016 in related European Patent Application No. 14 174 629.7.
Korean Office Action dated May 31, 2016 in related Korean Patent Application No. 10-2015-0151096.
Extended European Search Report dated May 3, 3016 in related European Patent Application No. 15181976.0.
Office Action dated Oct. 18, 2016 in related U.S. Appl. No. 14/755,486.

(56) References Cited

OTHER PUBLICATIONS

Office Action dated May 19, 2016 in related U.S. Appl. No. 14/685,998.
Office Action dated Jun. 24, 2016 in related U.S. Appl. No. 14/755,486.
Office Action dated Dec. 2, 2016 in related U.S. Appl. No. 14/685,998.
Office Action dated Mar. 23, 2017, in related U.S. Appl. No. 14/755,486.
Office Action dated Mar. 29, 2017, in related U.S. Appl. No. 14/685,998.
Korean Office Action dated Mar. 30, 2017, in corresponding Korean Patent Application No. 10-2015-0151096.
Korean Office Action dated Aug. 28, 2017, in corresponding Korean Patent Application No. 10-2015-0151096.
Notice of Allowance dated Jul. 13, 2017, in U.S. Appl. No. 14/755,486.
Office Action dated Dec. 27, 2017, in U.S. Appl. No. 14/685,998.

* cited by examiner

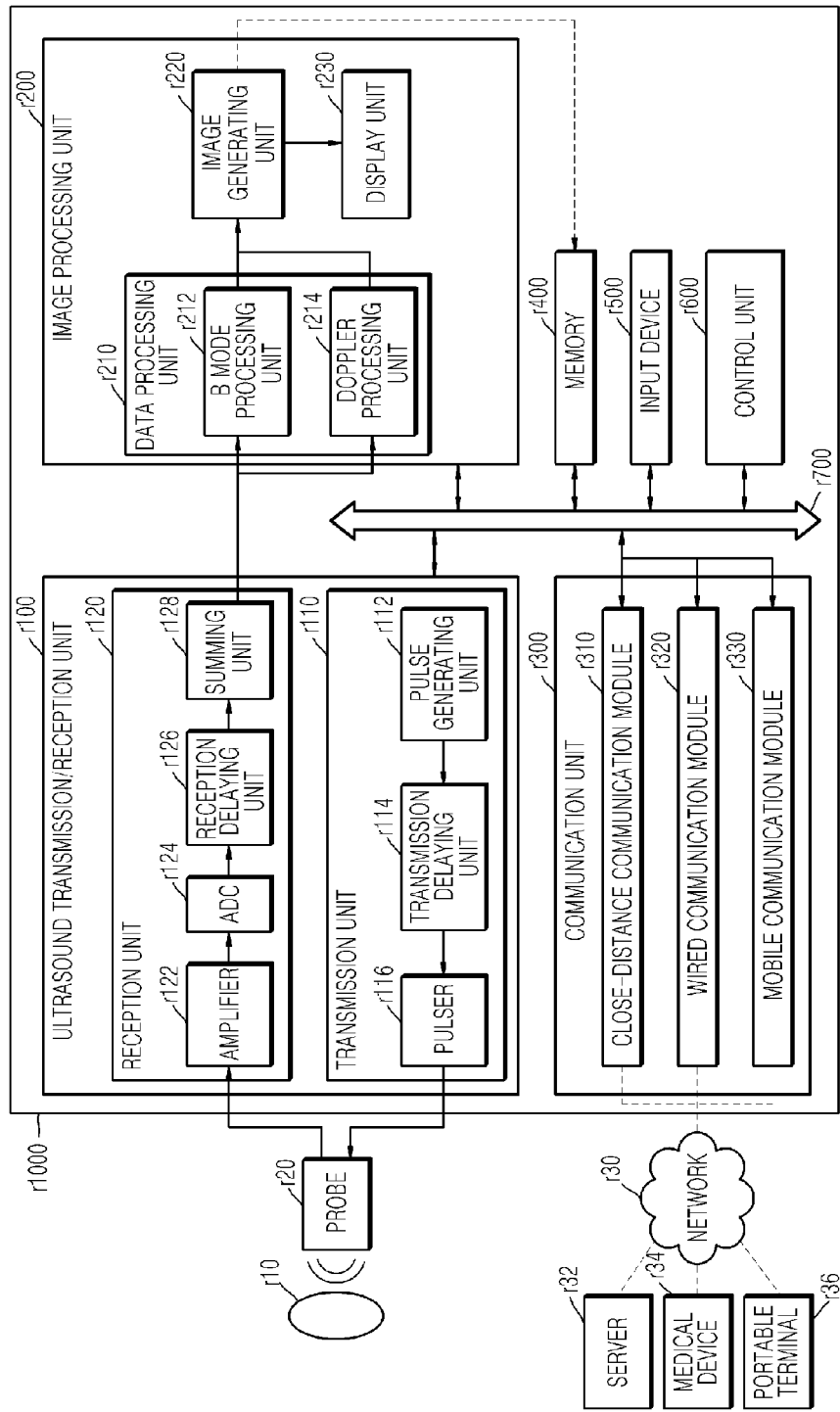

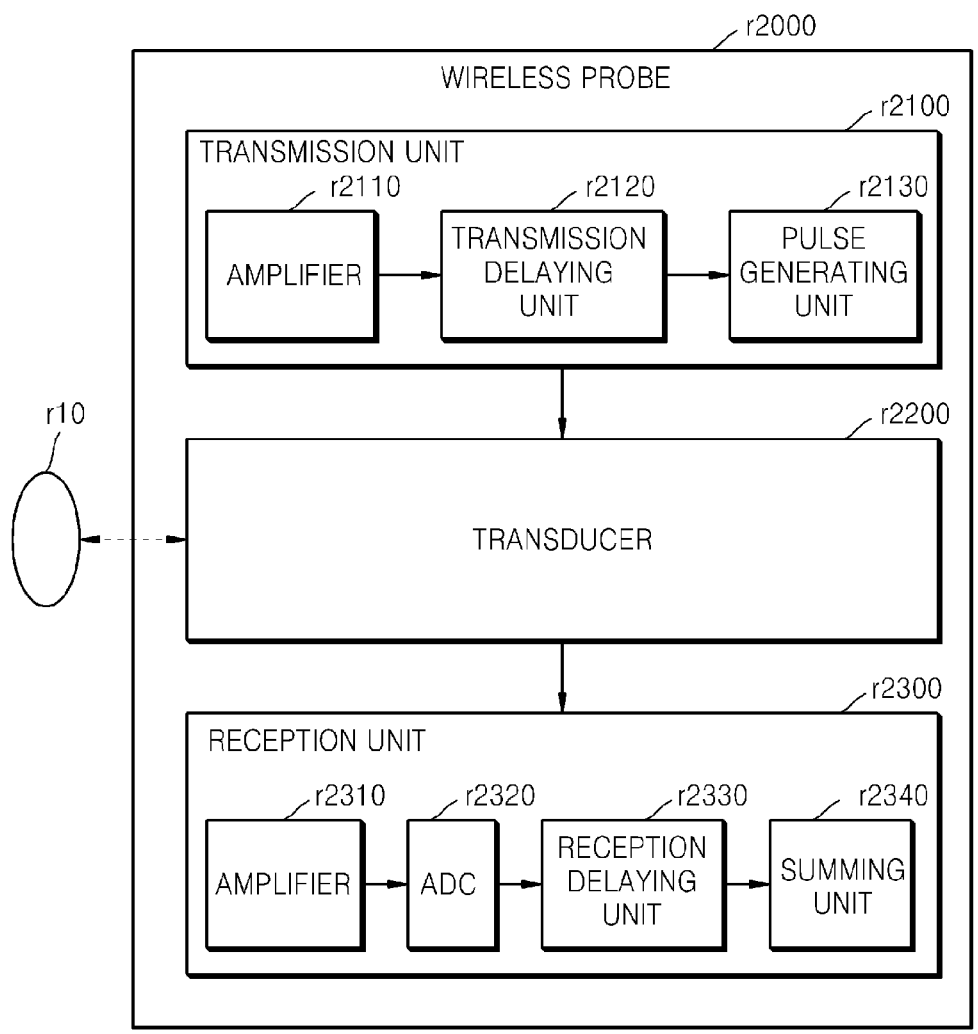

FIG. 9B
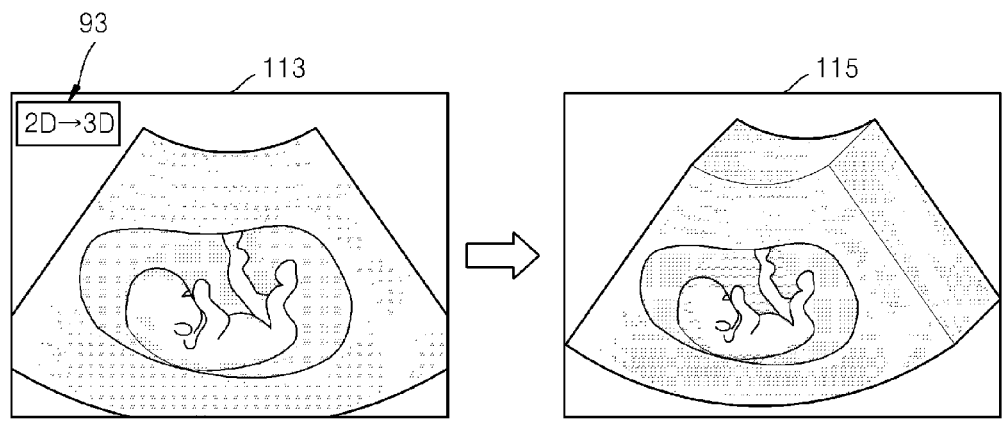
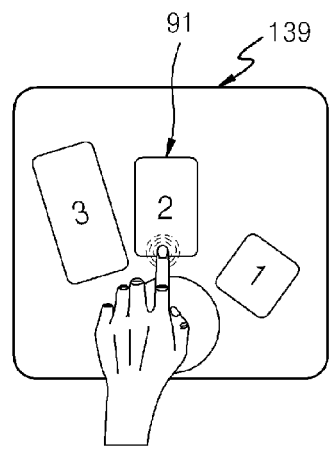

METHOD AND APPARATUS FOR CHANGING USER INTERFACE BASED ON USER MOTION INFORMATION

CROSS-REFERENCE TO RELATED PATENT APPLICATION

This application claims the benefit of Korean Patent Application No. 10-2013-0076586, filed on Jul. 1, 2013, in the Korean Intellectual Property Office, the disclosure of which is incorporated herein in its entirety by reference.

BACKGROUND

1. Field

The embodiments discussed herein relate to a method and an apparatus for changing a user interface based on user motion information.

2. Description of the Related Art

An ultrasound diagnosis device irradiates ultrasound signals generated by transducers of a probe to a target object and receives echo signals reflected from the target object, thereby obtaining images regarding the interior of the target object (e.g., tomography of soft tissues or blood flow). Particularly, an ultrasound diagnosis device may be used for medical purposes including observation of the interior of a target object, detection of foreign substances, and diagnosis of damage.

Such an ultrasound diagnosis device may display information regarding a target object in real-time. Furthermore, an ultrasound diagnosis device causes no radioactive exposure like X-ray, thus being highly safe. Therefore, an ultrasound diagnosis device is widely used together with other types of imaging diagnosis devices, including a computer tomography (CT) scanner, a magnetic resonance image (MRI) device, a nuclear medical diagnosis device, etc.

SUMMARY

The embodiments provide a method and an apparatus for changing a user interface (UI), which is used for diagnosis of a target object via a medical device, based on user motion information.

According to an aspect of the embodiments, there is provided a method of changing a user interface (UI), which is used for diagnosis of a target object via a medical device, based on user motion information, the method including obtaining motion information regarding a user; changing the UI based on the obtained motion information regarding the user; and displaying the changed UI.

The motion information regarding the user is obtained based on information regarding current location or position of a probe.

The information regarding current location of a probe includes at least one from among a current pointing direction of the probe and an angle of inclination and a height with respect to a predetermined reference point.

The motion information regarding the user is obtained based on biometric information regarding the user including at least one from among information regarding a fingerprint of the user, information regarding an iris of the user, and information regarding a face of the user.

The UI includes at least one from among a shortkey, a switch, a keyboard, and a trackball that indicate functions to be used for diagnosis of a target object.

In the changing of the UI based on the obtained motion information regarding the user, at least one from among shape, size, and location or position of the UI is changed based on the obtained motion information regarding the user.

At least one from among shape, size, and location of a UI is changed based on frequencies of accessing functions that are used during a diagnosis of a target object, according to an embodiment.

The UI may be edited based on externally input signals.

The UI is displayed via at least one from among a display unit on which a captured image of the target object is displayed and a control unit including display function.

The method further includes adjusting at least one from among height and angle of a control panel based on the motion information regarding the user.

The method further includes obtaining user identification information regarding the user; and storing the changed UI based on the obtained user identification information.

According to another aspect of the embodiments, there is provided an apparatus for changing a user interface (UI), which is used for diagnosis of a target object via a medical device, based on user motion information, the apparatus including a motion information obtaining unit for obtaining motion information regarding a user; a UI changing unit for changing the UI based on the obtained motion information regarding the user; and a display unit for displaying the changed UI.

The motion information obtaining unit further includes a sensing unit, and the motion information regarding the user is obtained based on information regarding a current location of a probe.

The information regarding current location of a probe includes at least one from among a current pointing direction of the probe and an angle of inclination and a height with respect to a predetermined reference point.

The motion information regarding the user is obtained based on biometric information regarding the user including at least one from among information regarding a fingerprint of the user, information regarding an iris of the user, and information regarding a face of the user.

The UI includes at least one from among a shortkey, a switch, a keyboard, and a trackball that indicate functions to be used for diagnosis of a target object.

The UI changing unit changes at least one from among shape, size, and location of the UI based on the obtained motion information regarding the user.

At least one from among shape, size, and location of a UI is changed based on frequencies of accessing functions that are used during a diagnosis of a target object, according to an embodiment.

The apparatus further including an external input receiving unit, wherein the UI may be edited by the UI changing unit based on externally input signals received via the external input receiving unit The apparatus further includes a control panel having a display function, wherein the UI is displayed via at least one from among the display unit and the control unit.

The apparatus further includes a control unit, wherein the control unit adjusts at least one from among height and angle of a control panel based on the motion information regarding the user.

The apparatus further includes an identification information obtaining unit for obtaining user identification information regarding the user; and a storage unit for storing a UI changed based on the user identification information.

According to another aspect of the embodiments there is provided a method including determining a use pattern by a user when using a medical device and providing an optimized layout of a user interface based on the use pattern, wherein the use pattern may be a user position when the user uses the medical device, the determining may include one of determining handedness, determining finger position, determining iris position, determining face position, determining probe motion, and frequency of function access and where the layout may be stored responsive to a user identity.

According to another aspect of the embodiments, there is provided a computer readable recording medium having recorded thereon a computer program for implementing the method.

BRIEF DESCRIPTION OF THE DRAWINGS

The above and other features and advantages of the embodiments will become more apparent by describing in detail exemplary embodiments thereof with reference to the attached drawings in which:

FIGS. 1A-1C, show an example of methods of diagnosing a target object by using a medical device in the related art;

FIG. 9B shows an example of using a UI changed according to an embodiment;

DETAILED DESCRIPTION

Expressions such as "at least one of," when preceding a list of elements, modify the entire list of elements and do not modify the individual elements of the list.

Hereinafter, the terms used in the specification will be briefly described, and then the embodiments will be described in detail.

The terms used in this specification are those general terms currently widely used in the art in consideration of functions in regard to the embodiments, but the terms may vary according to the intention of those of ordinary skill in the art, precedents, or new technology in the art. Also, specified terms may be selected by the applicant, and in this case, the detailed meaning thereof will be described in the detailed description of the embodiments. Thus, the terms used in the specification should be understood not as simple names but based on the meaning of the terms and the overall description of the embodiments.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, an "ultrasonic image" refers to an image of an object obtained using an ultrasonic wave.

Furthermore, in the present specification, "object" may include a person or an animal, or a part of a person or an animal. For example, the object may include the liver, the heart, the womb, the brain, a breast, the abdomen, or a blood vessel. Furthermore, the "object" may include a phantom. The phantom means a material having a volume that is approximately the intensity and effective atomic number of a living thing, and may include a sphere phantom having a property similar to a human body.

Furthermore, in the present specification, "user" refers to a medical professional, such as a doctor, a nurse, a medical laboratory technologist, and an engineer who repairs a medical apparatus, but the user is not limited thereto.

Embodiments now will be described more fully hereinafter with reference to the accompanying drawings, in which illustrative embodiments are shown.

FIG. 1 shows an example of methods of diagnosing a target object by using a medical device in the related art.

Figure 1A:
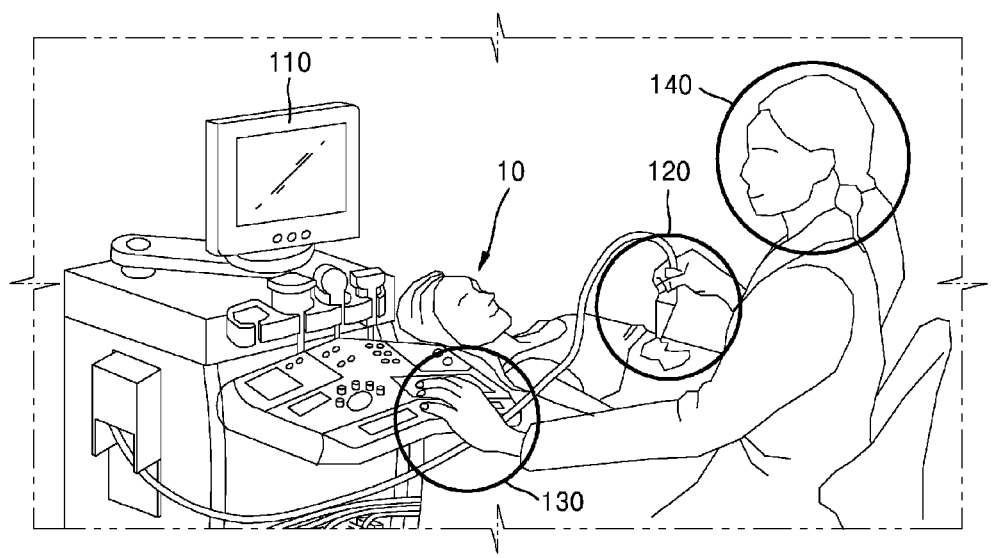

As shown in FIG. 1A, a user may diagnose a target object 10 by using a probe 120 of an ultrasound diagnosis device. In other words, the user may obtain a captured image regarding the target object 10 via a display unit 110 by operating the probe 120 and a control panel 130. For precise diagnosis of the target object 10, it is necessary to obtain a precisely captured image regarding the target object 10.

A relatively precisely captured image regarding the target object 10 may be obtained based on experiences of a user for using a medical device. However, in the case of capturing images regarding predetermined portions (e.g., the liver, the kidney, etc.) of the target object 10, it may be difficult for even an experienced user to operate a medical device based on locations for using the medical device (posture of the user) and to obtain a precisely captured image. For example, ease of operating a medical device may be irrelevant to experiences of a user based on a portion of a target object for imaging, a height of the target object, right hand or left hand preference of a user, frequencies of using predetermined buttons in a predetermined diagnosis, etc.

For example, if it is necessary to capture an image while the probe 120 is being moved in a large area, it may be difficult for a user to operate the 130 based on physical characteristics or a motion characteristic of the user. In other words, as the probe 120 is moved up, down, left, and right, a posture of the user will be changed, and, thus, the user may have to change posture again to smoothly operate the control panel 130. Furthermore, fixed height and position of the control panel 130 may be inconvenient to the user.

Furthermore, if an eye line 140 of a user is changed (e.g., the user has to look at the display unit 110 from a side) based on movement of the user, it may be difficult to obtain a precisely captured image regarding a target object or to recognize the image.

Therefore, it is necessary to automatically optimize an imaging environment of a medical device based on position at which a user uses the medical device for improving user convenience to operating the medical device. Furthermore, such an optimization of an imaging environment of a medical device enables precise imaging of a target object and reduction of imaging time.

Before embodiments are described, example configurations of an ultrasound diagnosis device related to an embodiment will be described below with reference to FIGS. 1B and 10. For convenience of explanation, a reference character r is added to components of the ultrasound diagnosis device.

FIG. 1B is a block diagram showing configuration of an ultrasound diagnosis device r1000 according to an embodiment.

The ultrasound diagnosis device r1000 according to an embodiment may include a probe r20, an ultrasound transmission/reception unit r100, an image processing unit r200, a communication unit r300, a memory r400, an input device r500, and a control unit r600, where the components stated above may be connected to one another via buses r700.

The ultrasound diagnosis device r1000 may be embodied not only as a cart type device, but also as a portable device. Examples of portable ultrasound diagnosis devices may include a PACS (picture archiving and communication system) viewer, a smart phone, a laptop computer, a personal digital assistant (PDA), and a tablet PC. However, the embodiments are not limited thereto.

The probe r20 transmits ultrasound waves to the target object r10 based on a driving signal applied by the ultrasound transmission/reception unit r100 and receives echo signals reflected by the target object r10. The probe r20 includes a plurality of transducers, and the plurality of transducers oscillate based on electric signals transmitted thereto and generate acoustic energy, that is, ultrasound waves. Furthermore, the probe r20 may be connected to the main body of the ultrasound diagnosis device r1000 wiredly or wirelessly. According to embodiments, the ultrasound diagnosis device r1000 may include a plurality of probes r20.

A transmission unit r110 supplies a driving signal to the probe r20 and includes a pulse generating unit r112, a transmission delaying unit r114, and a pulser r116.

The pulse generating unit r112 generates pulses for forming transmission ultrasound waves based on a predetermined pulse repetition frequency (PRF), and the transmission delaying unit r114 applies a delay time for determining transmission directionality to the pulses. Pulses to which a delay time is applied correspond to a plurality of piezoelectric vibrators included in the probe r20, respectively.

The pulser r116 applies a driving signal (or a driving pulse) to the probe r20 as a timing corresponding to each pulse to which a delay time is applied.

A reception unit r120 generates ultrasound data by processing echo signals received from the probe r20 and may include an amplifier r122, an analog-digital converter (ADC) r124, a reception delaying unit r126, and a summing unit r128.

The amplifier r122 amplifies echo signals in each channel, and the ADC r124 analog-digital converts the amplified echo signals.

The reception delaying unit r126 applies delay times for determining reception directionality to the digital-converted echo signals, and the summing unit r128 generates ultrasound data by summing the echo signals processed by the reception delaying unit r126.

The image processing unit r200 generates an ultrasound image by scan-converting ultrasound data generated by the ultrasound transmission/reception unit r100 and displays the ultrasound image.

Meanwhile, an ultrasound image may include not only a grayscale ultrasound image obtained by scanning a target object in an amplitude (A) mode, a brightness (B) mode, and a motion (M) mode, but also a blood flow Doppler image showing flow of blood (aka a color Doppler image), a tissue Doppler image showing movement of tissues, and a spectral Doppler image showing moving speed of a target object as a waveform.

A B mode processing unit r212 extracts B mode components from ultrasound data and processes the B mode components.

An image generating unit r220 may generate an ultrasound image indicating signal intensities as brightness based on the extracted B mode components.

Similarly, a Doppler processing unit r214 may extract Doppler components from ultrasound data, and the image generating unit r220 may generate a Doppler image indicating movement of a target object as colors or waveforms based on the extracted Doppler components.

The image generating unit r220 according to an embodiment may generate a 3-dimensional (3D) ultrasound image via volume-rendering of volume data and may also generate an elasticity image which visualizes deformation of a target object r10 due to a pressure. Furthermore, the image generating unit r220 may display various additional information in an ultrasound image by using text and graphics. Meanwhile, the generated ultrasound image may be stored in the memory r400.

A display unit r230 displays the generated ultrasound image. The display unit r230 may display not only an ultrasound image, but also various information processed by the ultrasound diagnosis device r1000 in a screen image via a graphic user interface (GUI). Meanwhile, the ultrasound diagnosis device r1000 may include two or more display units r230 according to embodiments.

The communication unit r300 is wiredly or wirelessly connected to a network r30 and communicates with an external device or a server. The communication unit r300 may exchange data with a hospital server or another medical device in a hospital that is connected with a picture archiving and communications system (PACS). Furthermore, the communication unit r300 may perform data communication according to the digital imaging and communications in medicine (DICOM) standard.

The communication unit r300 may transmit and receive data related to diagnosis of a target object, e.g., an ultrasound image, ultrasound data, and Doppler data of the target object, via the network r30 and may also transmit and receive medical images obtained via other medical devices, e.g., a CT image, a MR image, and an X-ray image. Furthermore, the communication unit r300 may receive information related to a diagnosis history or a treatment schedule of a patient from a server and utilizes the information for diagnosing the patient. Furthermore, the communication unit r300 may perform data communication not only with a server or a medical device in a hospital, but also with a portable terminal of a doctor or a patient.

The communication unit r300 is connected to the network r30 wiredly or wirelessly and may exchange data with a server r32, a medical device r34, or a portable terminal r36. The communication unit r300 may include one or more components that enable communication with external devices, e.g., a close-distance communication module r310, a wired communication module r320, and a mobile communication module r330.

The close-distance communication module r310 may refer to a module for close-distance communication within a predetermined distance. Examples of close-distance communication techniques according to an embodiment may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC). However, the embodiments are not limited thereto.

The wired communication module r320 refers to a module for communication using electric signals or optical signals. Examples of wired communication techniques according to an embodiment may include a pair cable, a coaxial cable, an optical fiber cable, and an Ethernet cable.

The mobile communication module r330 transmits and receives wireless signals with at least one from among a station, an external terminal, and a server on a mobile communication network. Here, the wireless signals may include voice call signals, video call signals, or various types of data for transmission and reception of text/multimedia messages.

The memory r400 stores various data processed by the ultrasound diagnosis device r1000. For example, the memory r400 may store medical data related to diagnosis of a target object, such as ultrasound data and an ultrasound image that are input or output and may also store algorithms or programs to be executed in the ultrasound diagnosis device r1000.

The memory r400 may be embodied as any of various storage media, e.g., a flash memory, a hard disk drive, an EEPROM, etc. Furthermore, the ultrasound diagnosis device r1000 may utilize a web storage or a cloud server that functions as the memory r400 online.

The input device r500 refers to a means via which a user inputs data for controlling the ultrasound diagnosis device r1000. The input device r500 may include hardware components, such as a keypad, a mouse, a touch panel, a touch screen, and a jog switch. However, the embodiments are not limited thereto, and the input device r500 may further include various other input means including an electrocardiogram measuring module, a respiration measuring module, a voice recognition sensor, a gesture recognition sensor, a fingerprint recognition sensor, an iris recognition sensor, a depth sensor, a distance sensor, etc.

The control unit r600 may control overall operations of the ultrasound diagnosis device r1000. In other words, the control unit r600 may control operations among the probe r20, the ultrasound transmission/reception unit r100, the image processing unit r200, the communication unit r300, the memory r400, and the input device r500 shown in FIG. 1.

All or some of the probe r20, the ultrasound transmission/reception unit r100, the image processing unit r200, the communication unit r300, the memory r400, the input device r500, and the control unit r600 may be operated by software modules. However, the embodiments are not limited thereto, and some of the components stated above may be operate by hardware modules.

Furthermore, at least one of the ultrasound transmission/reception unit r100, the image processing unit r200, and the communication unit r300 may be included in the control unit r600. However, the embodiments are not limited thereto.

FIG. 1C is a block diagram showing configuration of a wireless probe r2000 according to an embodiment.

As described above with reference to FIG. 1B, the wireless probe r2000 may include a plurality of transducers, and, according to embodiments, may include a part or all of the ultrasound transmission/reception unit r100 shown in FIG. 1B.

The wireless probe r2000 according to the embodiment shown in FIG. 1C includes a transmission unit r2100, a transducer r2200, and a reception unit r2300. Since descriptions thereof are given above with reference to FIG. 1, detailed descriptions thereof will be omitted. Meanwhile, according to the embodiments, the wireless probe r2000 may selectively include a reception delaying unit r2330 and a summing unit r2340.

The wireless probe r2000 may transmit ultrasound signals to the target object r10, receive echo signals, generate ultrasound data, and transmit the ultrasound data to the ultrasound diagnosis device r1000 shown in FIG. 1 wirelessly.

FIG. 2 is a schematic diagram showing a method of changing a user interface (UI) used for diagnosis of a target object via a medical device based on information regarding motion of a user, according to an embodiment.

Figure 2A:
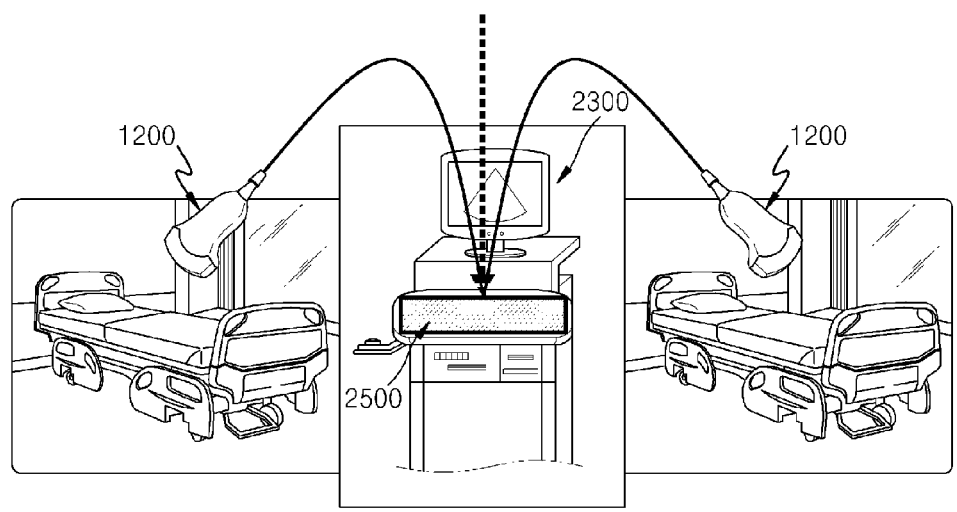
FIGS. 2A-2B are a schematic diagram showing a method of changing a user interface (UI) used for diagnosis of a target object via a medical device based on information regarding motion of a user, according to an embodiment.

As shown in FIG. 2A, it may be determined whether a user uses a probe 1200 left-handedly or right-handedly by detecting a direction of motion of a cable connected to the probe 1200. For example, if a user is left-handed, the user may use the probe 1200 left-handedly. In the same regard, if a user is right-handed, the user may use the probe 1200 right-handedly As described above, according to a user's aspect of using the probe 1200, a different UI may be provided on a control panel.

Figure 2B:
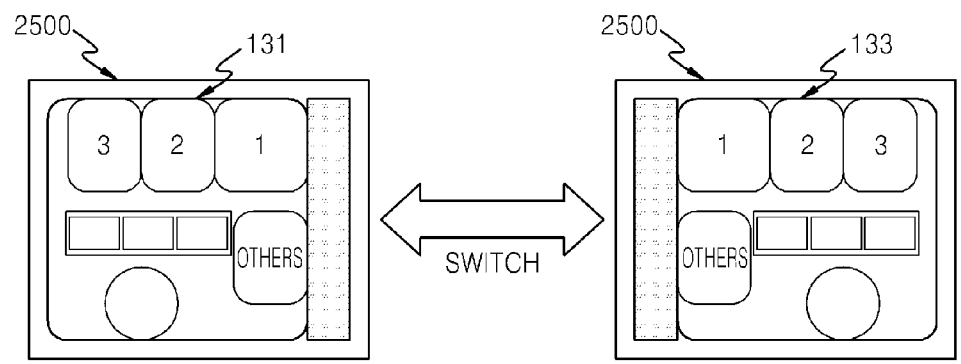

For example, as shown in FIG. 2B, if a user is right-handed, it may be convenient for the user to locate a target object to the right and operate the probe 1200 right-handedly. Therefore, if a user is right-handed, it is necessary to provide buttons and a trackball layout that are included in a control panel 2500 and are to be used for imaging operation as a right-handed UI pattern 131.

Furthermore, if a user is left-handed, it may be convenient for the user to locate a target object to the left and operate the probe 1200 left-handedly. In other words, if a user is left-handed, a left-handed UI pattern 133 may be provided on a control panel 2500.

Furthermore, the right-handed UI pattern 131 and the left-handed UI pattern 133 on the control panel 2500 may be switched based on information regarding motion of a user including current location or position of the probe 1200 and change of location of the probe 1200.

Figure 3:
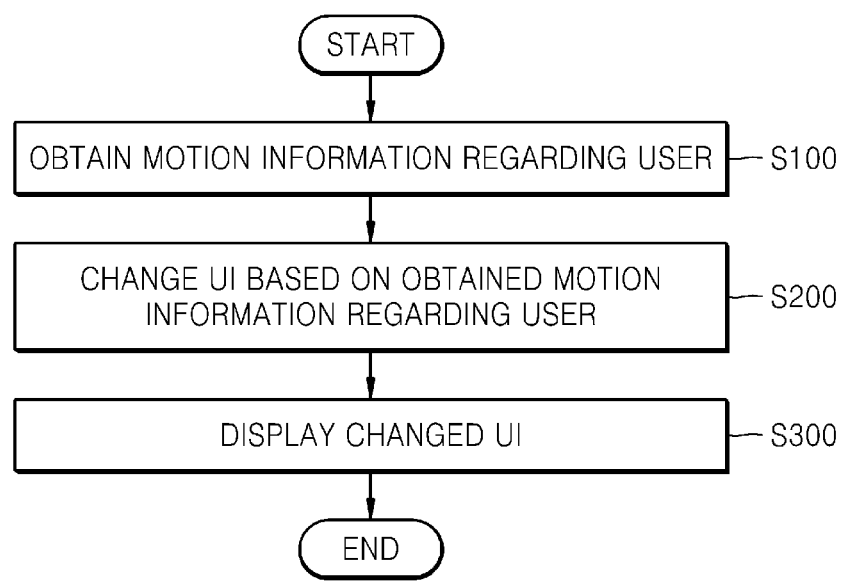
FIG. 3 is a flowchart showing a method of changing a UI used for diagnosis of a target object via a medical device based on information regarding motion of a user, according to an embodiment.

FIG. 3 is a flowchart showing a method of changing a UI used for diagnosis of a target object via a medical device based on information regarding motion of a user, according to an embodiment.

The method of changing a UI used for diagnosis of a target object via a medical device based on information regarding motion of a user, according to an embodiment may include an operation S100 for obtaining information regarding motion of a user, an operation S200 for changing the UI by using the information regarding motion of the user, and an operation S300 for displaying the changed UI.

Information regarding motion of a user may be obtained according to an embodiment (the operation S100).

A UI displaying buttons and trackballs to be used for an imaging operation may be changed by using the information regarding motion of the user (the operation S200). The change of the UI may include optimization of medical device imaging environments, such that a user may easily operate a medical device.

As described above, the change of a UI may include switching UI arrangement or layout based on left-handedness or right-handedness of a user and changing arrangement and size of the UI based on frequencies of using respective buttons.

The changed UI according to an embodiment may be provided to the user via a display unit (the operation S300).

Information regarding motion of a user according to an embodiment may be obtained based on location of a probe and biometric information regarding a user. Detailed descriptions thereof will be given below with reference to FIGS. 4 and 5.

Figure 4:
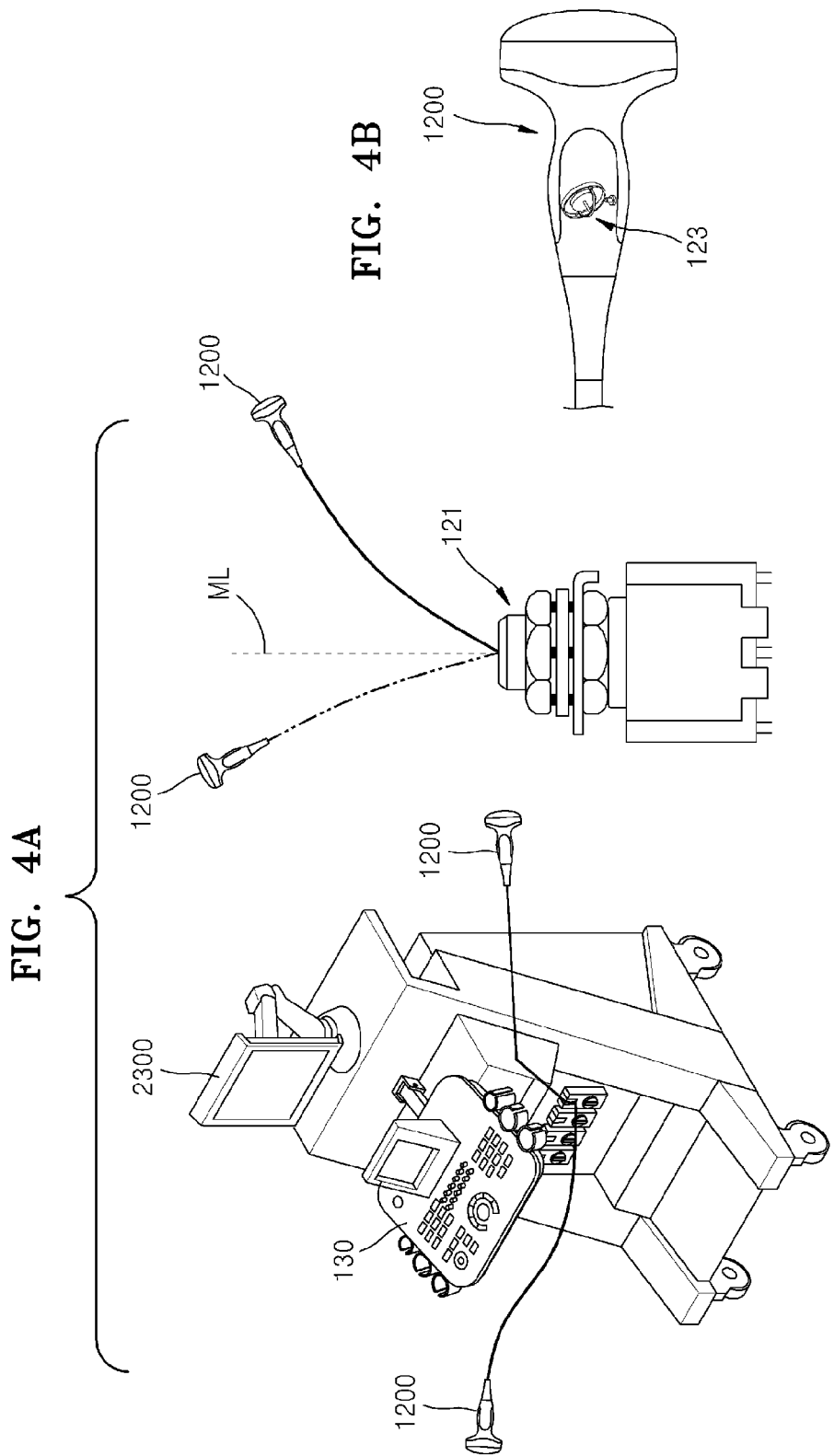
FIGS. 4A-4B show an example of obtaining information regarding motion of a user according to an embodiment.

FIG. 4 shows an example of obtaining information regarding motion of a user according to an embodiment.

According to an embodiment, information regarding motion of a user may be obtained based on information regarding current location of the probe 1200.

The information regarding current location of the probe 1200 according to an embodiment may include at least one from among current pointing direction of the probe 1200, an angle of inclination with respect to a predetermined reference point, and a height.

For example, the information regarding current location of the probe 1200 may be obtained based on a pointing direction of the probe 1200. For example, information regarding current pointing direction of the probe 1200 may be obtained via a predetermined sensor 121 that is included in the probe 1200 (e.g., included at an end of the probe 1200 to be connected to an ultrasound device) or embedded in an ultrasound device to which the probe 1200 is to be connected.

The predetermined sensor 121 may be configured to determine a pointing direction of the probe 1200 based on an orientation that a cable connected to the probe 1200 faces or take from a relative to a reference line (e.g., the center line ML of the predetermined sensor 121).

For example, a pointing direction of the probe 1200 may be determined based on the toggle switch type sensor 121. As shown in FIG. 4A, if the probe 1200 is biased to the right from the center line ML, it may be determined that information regarding current location or position of the probe 1200 points to the right from an ultrasound device including a display unit 2300 and a control panel 2500. In other words, information indicating that the probe 1200 is located to the right from the ultrasound device may be obtained.

Furthermore, as shown in FIG. 4A, if the probe 1200 is biased to the left from the center line ML, it may be determined that information regarding current location of the probe 1200 points to the left from an ultrasound device including the display unit 2300 and the control panel 2500. In other words, information indicating that the probe 1200 is located to the left from the ultrasound device may be obtained.

Furthermore, if the probe 1200 according to an embodiment is a wireless probe, the predetermined sensor 121 may be configured to detect global positioning system (GPS) coordinates of the wireless probe 1200 via a wireless communication.

Furthermore, according to an embodiment, information regarding current location of the probe 1200 may include at least one from between an angle of inclination and a height with respect to a predetermined reference point.

As shown in FIG. 4B, the probe 1200 may include a sensor 123 for obtaining information regarding an angle of inclination or information regarding height. The sensor 123 may include a gyro sensor, a height sensor, etc.

For example, information regarding current location or position of the probe 1200 may be obtained as information regarding an angle of inclination with respect to a predetermined reference point. The predetermined reference point may include the ground surface on which a medical device is located, a patient table, or initial location of the probe 1200 (e.g., location of the probe 1200 when the probe 1200 is attached to an ultrasound device), for example.

Current motion of a patient may be estimated in correspondence to the information regarding an angle of inclination. For example, it may be estimated that motion of the probe 1200 becomes larger as a change of the angle of inclination becomes larger, and information regarding motion regarding range of angles of motion of a user operating the probe 1200 based on estimated movement of the probe 1200.

For example, the ground surface (or a patient table) and the probe 1200 may form an angle therebetween up to 90 degrees (e.g., when the probe 1200 is located perpendicular to the ground surface). A user may move the probe 1200 in a predetermined direction and at a predetermined angle during an imaging operation. The angle formed between the probe 1200 and the ground surface may be within a predetermined range (e.g., from 0 degree to 90 degrees). For example, if a user wants to obtain an ultrasound image of the liver of a patient, the probe 1200 may be moved by a user in a range between being parallel to the ground surface (e.g., the angle between the probe 1200 and the ground surface is 0 degree) and being perpendicular to the ground (e.g., the angle between the probe 1200 and the ground surface is 90 degrees).

In other words, when the probe 1200 is initially located or positioned parallel to the ground surface and the probe 1200 is then moved in a direction perpendicular to the ground surface, change of an angle of inclination may be the maximum, and movement of the probe 1200 may be estimated as the maximum. Based on the estimated movement of the probe 1200, motion information indicating that movement of a person operating the probe 1200 is also the maximum may be obtained.

Furthermore, in a similar regard, an angle of inclination at the initial location of the probe 1200 at which the probe 1200 is attached to an ultrasound device may be obtained as information regarding the current location of the probe 1200.

For example, the sensor 123 according to an embodiment may indicate directions to the right or to the east from the sensor 123 as positive angles and directions to the left or the west from the sensor 123 as negative angles. However, the embodiments are not limited thereto.

Therefore, if the probe 1200 is currently biased to the right from the initial location, a positive angle of inclination may be detected by the sensor 123, and thus information indicating that the probe 1200 is at a location or position corresponding to an angle of inclination detected to the right from the sensor 123. Furthermore, if the probe 1200 is currently biased to the left from the initial location, a negative angle of inclination may be detected by the sensor 123, and thus information indicating that the probe 1200 is at a location corresponding to an angle of inclination detected to the left from the sensor 123.

Furthermore, information regarding current location of the probe 1200 may be obtained as information regarding height with respect to a predetermined reference point. The predetermined reference point may include the ground surface, a patient table, or an initial location of the probe 1200 (e.g., location of the probe 1200 when the probe 1200 is attached to an ultrasound device), for example. In this case, the sensor 123 may be a height sensor.

For example, the sensor 123 may detect that the probe 1200 is located about 120 cm from the ground surface. Furthermore, the sensor 123 may detect that the probe 1200 is located about 5 cm lower than the height corresponding to the initial state in which the probe 1200 is attached to an ultrasound device. In other words, information regarding heights with respect to predetermined reference points may be obtained as information regarding current location or position of the probe 1200.

Motion information indicating a change of height or posture of a user operating the probe 1200 may be obtained based on information regarding height of the probe 1200 (e.g., change of height) according to an embodiment.

Figure 5:
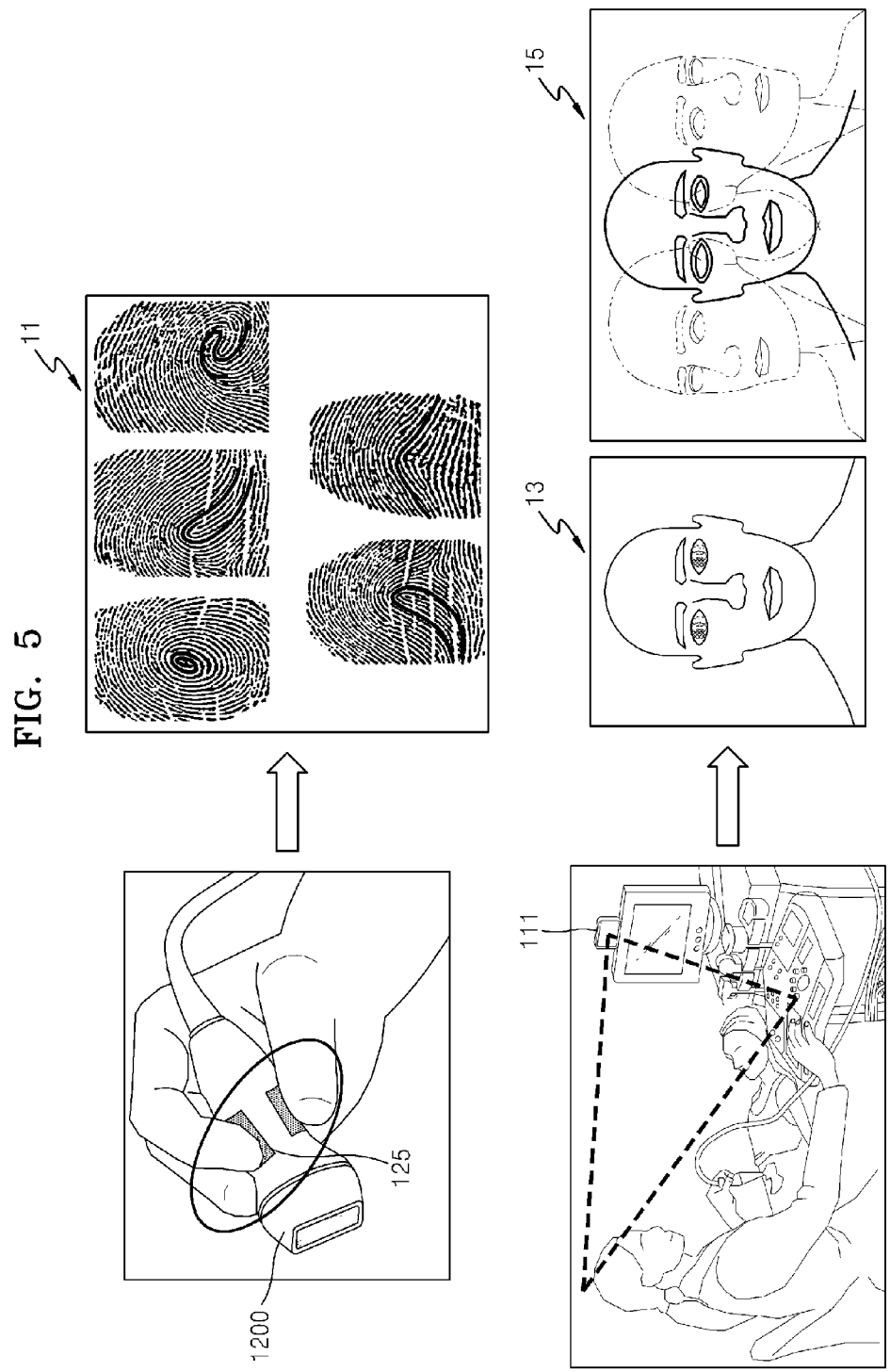
FIG. 5 shows an example of motion information regarding a user obtained according to another embodiment.

FIG. 5 shows an example of motion information regarding a user obtained according to another embodiment.

Motion Information regarding a user according to the present embodiment may be obtained based on biometric information regarding the user including at least one from among information regarding a fingerprint of the user, information regarding an iris of the user, and information regarding a face of the user.

Motion Information regarding a user according to the present embodiment may be obtained based on information regarding a fingerprint of the user.

For example, based on fingerprint information 11 regarding a user obtained via a sensor 125 embedded in the probe 1200, it may be determined whether the user is currently grabbing the probe 1200 with the left hand or the right hand.

In other words, motion information or finger position information indicating whether the user is using the probe 1200 with the left hand or the right hand may be obtained based on the fingerprint information 11 obtained via the sensor 125 embedded in the probe 1200.

For example, if the fingerprint information 11 corresponds to the fingerprint of the right thumb or right forefinger of a user, it is determined that the user is currently grabbing the probe 1200 with the right hand, and, thus, motion information indicating that the user is using the probe 1200 with the right hand may be obtained.

Furthermore, if the fingerprint information 11 corresponds to the fingerprint of the left thumb or left forefinger of a user, it is determined that the user is currently grabbing the probe 1200 with the left hand, and, thus, motion information indicating that the user is using the probe 1200 with the left hand may be obtained.

Furthermore, according to an embodiment, it may be determined who a user currently using the probe 1200 is based on the fingerprint information 11 obtained via the sensor 125 embedded in the probe 1200. In this case, the fingerprint information 11 may be utilized as user identification information (e.g., an ID).

Information regarding motion of a user according to an embodiment may be obtained based on at least one from among iris information 13 and face information 15 of a user.

As shown in FIG. 5, at least one from between the iris information 13 and the face information 15 may be obtained via a sensor 111 arranged on an ultrasound device. The sensor 111 may be arranged nearby a display unit 2300 of an ultrasound device. However, the embodiments are not limited thereto.

Furthermore, the sensor 111 may either perform both iris recognition and face recognition simultaneously or be embodied as independent sensors for iris recognition and face recognition.

According to an embodiment, the iris information 13 regarding a user may be obtained via the sensor 111 according to an embodiment. The iris information 13 may include user identification information indicating who a current user is and information regarding current locations or positions of irises of the current user. For example, by recognizing irises of a current user via the sensor 111, information regarding identification of the current user may be obtained.

Furthermore, a current line of sight of a user may be determined based on information regarding current locations of irises obtained via the sensor 111, and motion information regarding the user may be obtained based on the current line of sight of the user. In other words, information regarding a current posture of the user may be obtained based on whether irises are more biased to the left or to the right. However, the embodiments are not limited thereto.

For example, if irises are substantially biased to the left in eyes of a user, it may be determined that the upper body of the user faces to the right. In other words, it may be determined that the user is operating the probe 1200 with the right hand.

Similarly, if irises are substantially biased to the right in eyes of a user, it may be determined that the upper body of the user faces to the left. In other words, it may be determined that the user is operating the probe 1200 with the left hand.

According to an embodiment, the face information 15 of a user may be obtained via the sensor 111. The face information 15 may include user identification information indicating who the user is and information regarding a direction the face of the user faces. For example, information regarding who the user is may be obtained by recognizing face feature points and face silhouette of the user via the sensor 111.

Furthermore, main face of the user may be determined by using the information regarding a direction the face of the user faces obtained via the sensor 111, and motion information regarding the user may be obtained based on the main face of the user. In other words, a current main face of the user may be determined based on area of a face of the user, and information regarding a current posture of the user may be obtained from the determined main face.

For example, when an area of a right face of a user is compared to an area of a left face of the user and it is determined that the left face of the user is larger than the right face of the user, it may be determined that the upper body of the user faces to the right. In other words, it may be determined that the user is operating the probe 1200 with the right hand.

Similarly, when an area of a right face of a user is compared to an area of a left face of the user and it is determined that the right face of the user is larger than the left face of the user, it may be determined that the upper body of the user faces to the left. In other words, it may be determined that the user is operating the probe 1200 with the left hand.

Furthermore, motion information regarding a user may be obtained by using the iris information 13 and the face information 15 of the user. For example, when the area of the right face of a user is compared to the area of the left face of the user and it is unclear which of the left face and the right face is larger than the other, information regarding irises of the user may be further utilized as described above for obtaining the motion information regarding the user.

Figure 6:
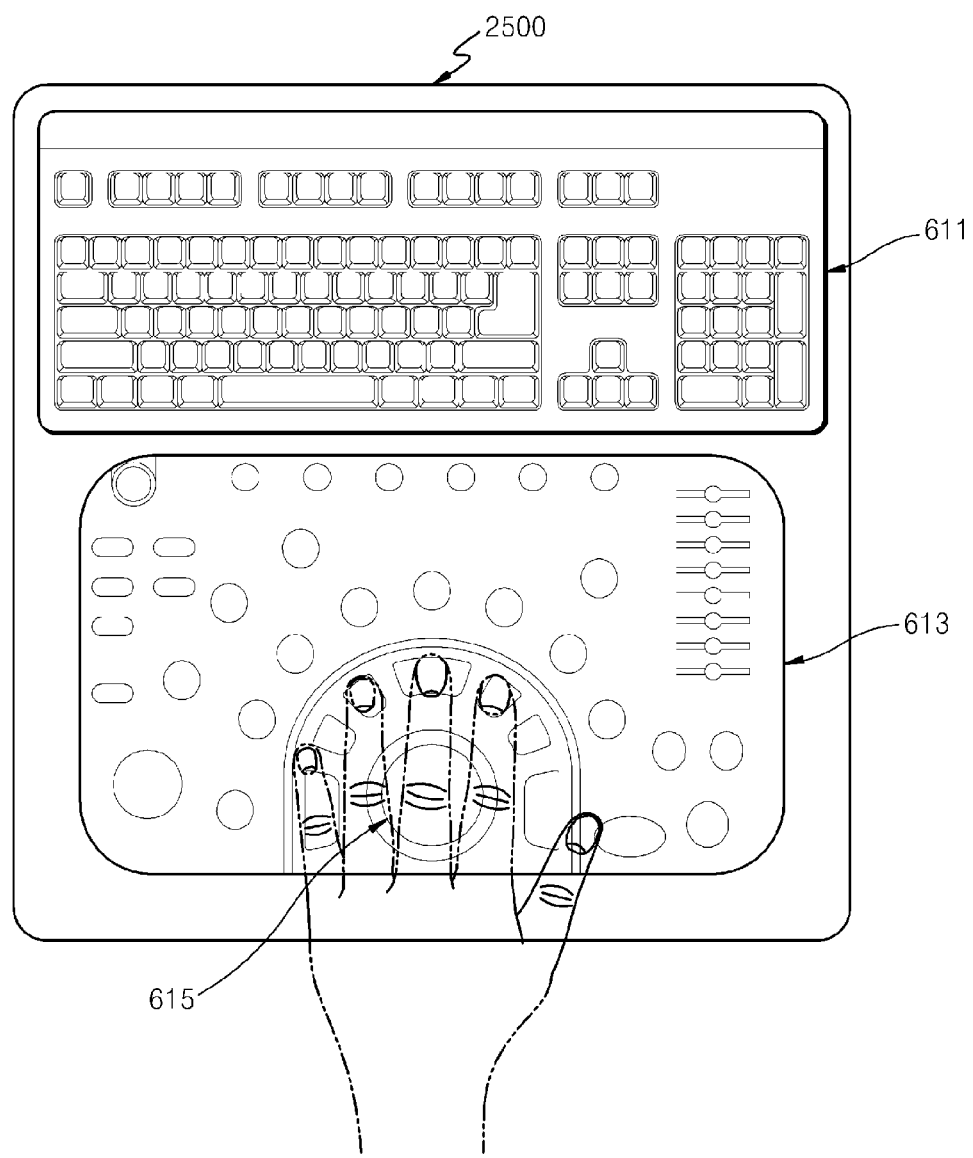
FIG. 6 shows an example of a UI that may be changed and provided according to an embodiment.

FIG. 6 shows an example of a UI that may be changed and provided according to an embodiment.

As shown in FIG. 6, UIs (e.g., 611 through 615) for displaying functions of a medical device may be displayed.

A UI according to an embodiment may include at least one from among a shortkey, a switch, a keyboard, and a trackball that indicate functions to be used for diagnosis of a target object.

A UI according to an embodiment may include a keyboard type UI 611 for inputting letters and numbers in relation to imaging of a target object, at least one button or switch type UI 613 and trackball type UI 615 indicating predetermined functions, such as image zoom in/out, resolution control, switch between a 2D image and a 3D image, etc.

At least one from among the keyboard type UI 611, the button or switch type UI 613, and the trackball type UI 615 may be provided as a virtual UI layout.

In other words, a UI according to an embodiment is not necessarily in the physical form and may be virtually embodied to indicate a predetermined function in the form of letters, numbers, and images on the display unit 2300 or the control panel 2500.

FIG. 7 shows an aspect in which a UI is changed and provided based on motion information regarding a user according to an embodiment. For convenience of explanation, the UI is simplified.

The operation S200 for changing a UI by using motion information regarding a user according to an embodiment may include changing at least one from among shape, size, and location or position of the UI based on motion information regarding the user.

Figure 7A:
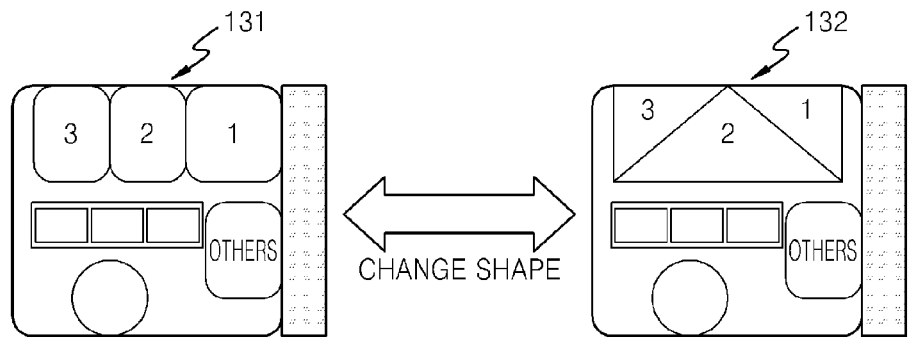
FIGS. 7A-7C show an aspect that a UI is changed and provided based on motion information regarding a user according to an embodiment.

As shown in FIG. 7A, a shape of a UI may be changed based on the motion information regarding the user.

For example, if moving a range of the probe 1200 significantly increases (that is, if motion of a user significantly increases), it may be inconvenient for the user to touch the UI 611 through 615. In other words, a hand of the user may not reach the UI or it may be difficult for the user to operate the UI.

In this case, according to an embodiment, the shape of the UI may be changed for improving user convenience. For example, the shape of a UI (1 through 3 of 131), which is simplification of the keyboard type UI 611 or the button or switch type UI 613 of FIG. 6, may be changed and the changed UI 132 may be provided. For example, if the user uses a button 2 more frequently than buttons 1 and 3 during an imaging operation, shape of the button 2 may be changed to a triangle in which the base is longer than the other sides, such that the user may access the button 2 more easily. In other words, a change may be made, such that the button 2 is larger than the button 1 or the button 3.

Furthermore, according to an embodiment, locations or layout of the buttons 1 through 3 may be changed. For example, the UI may be changed, such that the buttons 1 through 3 are arranged in the order of the button 3, the button 1, and the button 2. In this case, the button 1 may be the most frequently used button and may have a triangular shape in which the base is longer than the other sides. However, the embodiments are not limited thereto.

Figure 7B:
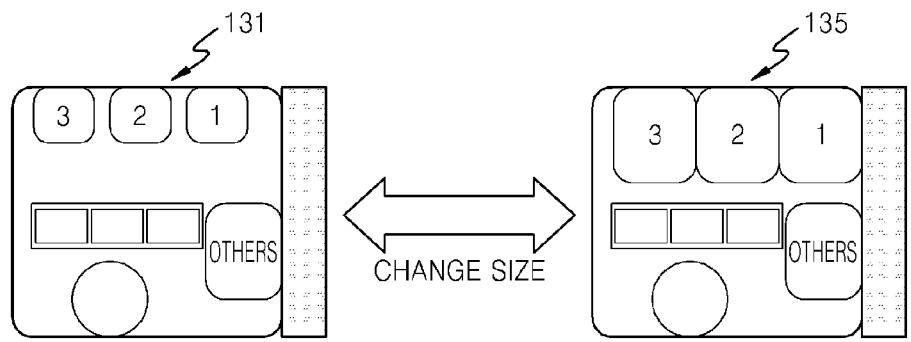

Furthermore, as shown in FIG. 7B, size of a UI may be changed based on motion information regarding a user.

As described above, when motion of a user increases, a changed UI 135 in which sizes of buttons of the UI pattern 131 may be overall or partially increased and decreased may be provided, such that the user may easily access the buttons.

For example, sizes of the buttons 1 through 3 may be increased for easier access of a user. Similarly, locations of the buttons 1 through 3 may be changed to be closer to the user for easier access of the user.

Figure 7C:
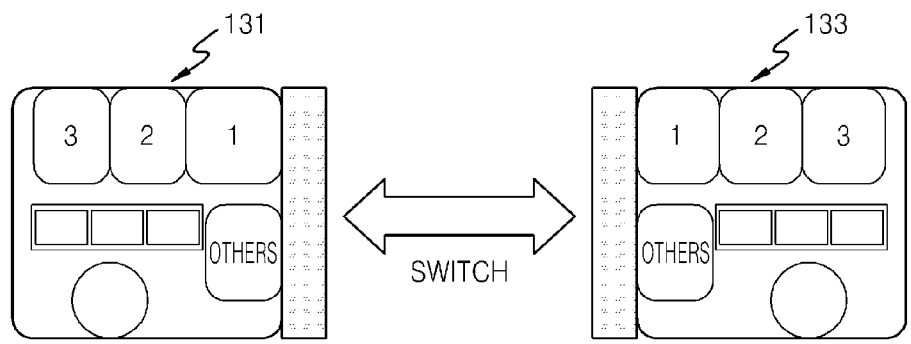

Furthermore, as shown in FIG. 7C, different UI patterns may be provided based on physical features of a user.

For example, if the user is right-handed, the right-handed UI pattern 131 may be provided. Furthermore, if the user is left-handed, the left-handed UI pattern 133 may be provided. The right-handed UI pattern 131 and the left-handed UI pattern 133 may be symmetrical to each other and may be switched based on motion information regarding the user as described above.

Figure 8A:
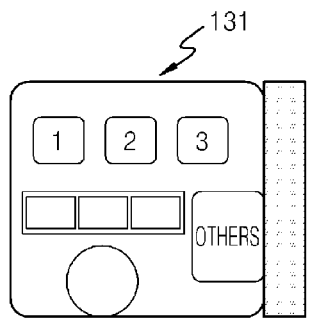
FIGS. 8A-8C shows an aspect in which a UI is changed and provided based on motion information regarding a user according to another embodiment.

FIG. 8 shows an aspect in which a UI is changed and provided based on motion information regarding a user according to another embodiment.

At least one from among shape, size, and location of a UI may be changed based on frequencies of accessing functions that are used during a diagnosis of a target object, according to an embodiment.

For example, at least one from among shape, size, and location of the UI pattern 131 of FIG. 7, which is a simplified form of the keyboard type UI 611 or the button or switch type UI 613 of FIG. 6, may be changed (a UI pattern 137 or a UI pattern 139) based on frequencies of accessing functions that are used during a diagnosis of a target object. For convenience of explanation, it is assumed that the UI pattern 131 is the basic pattern that may be provide by a medical device.

Figure 8B:
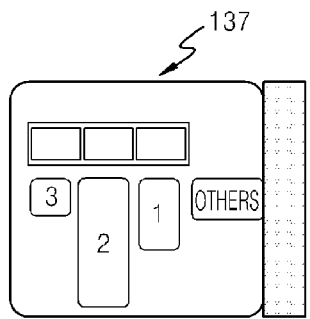

For example, for a predetermined diagnosis item, a trackball may not be used, and a function corresponding to a second button from among button type UIs indicated as first through third buttons may be used more frequently than the others. In this case, as shown in FIG. 8B, a circular UI corresponding to a trackball function may be omitted, and a UI corresponding to the second button may be changed to have the largest size.

In other words, UIs that are not used or less frequently used by a user may be omitted and the size of a frequently used UI may be increased, thereby improving UI accessibility and convenience of a user operating a medical device.

Figure 8C:
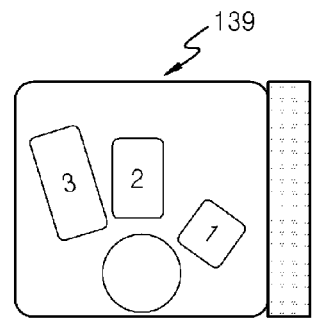

As another example, if a user frequently uses a trackball and a third button (e.g., zoom in/out function) from among button type UIs for a predetermined diagnosis item, sizes of the circular UI corresponding to a trackball and the third button from among the button type UIs in the basic pattern 131 may be increased (the UI pattern 139), as shown in FIG. 8C.

Furthermore, UIs may be arranged in a radial shape in correspondence to fingers of a user as shown in the pattern 139 as shown in FIG. 8C. However, the embodiments are not limited thereto.

Furthermore, frequencies of using functions may differ based on types of diagnosis, different UI patterns may be provided in correspondence to different types of diagnosis.

For example, frequencies of using functions provided by an ultrasound device may differ based on types of diagnosis including heart ultrasound diagnosis, liver ultrasound diagnosis, abdominal ultrasound diagnosis, Pelvic ultrasonography, Doppler ultrasound diagnosis, etc. For example, the image zoom in/out function and the trackball function may be frequently used for a heart ultrasound diagnosis, whereas a resolution controlling function may be more frequently used than the image zoom in/out function and the trackball function for a liver ultrasound diagnosis.

In other words, for heart ultrasound diagnosis, sizes of a UI for performing image zoom in/out function and a UI for performing trackball function may be larger than other UIs and may be arranged at the center of the control panel 2500, for example.

On the contrary, for liver ultrasound diagnosis, sizes of a UI for performing image zoom in/out function and a UI for performing trackball function may be reduced or the UI for performing image zoom in/out function and the UI for performing trackball function may be omitted, whereas a UI for performing a resolution controlling function may be larger than other UIs and may be arranged at the center of the control panel 2500.

Figure 9A:
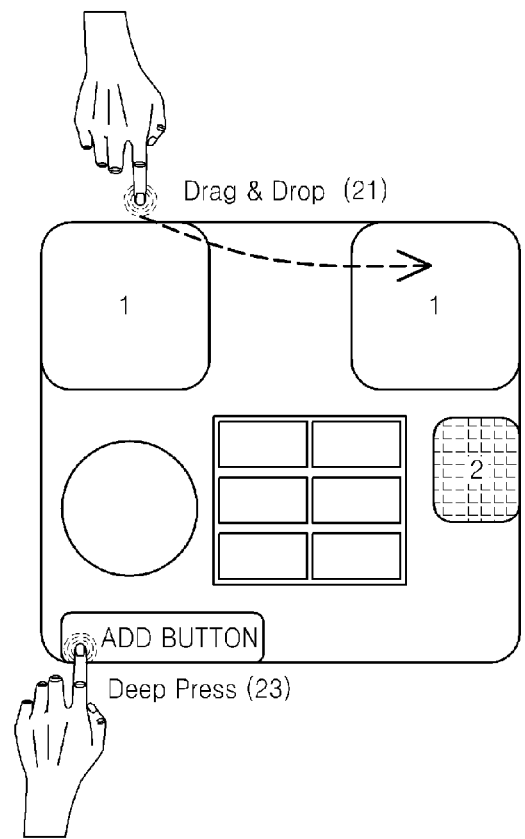
FIG. 9A shows a example of editing a UI according to an embodiment.

FIG. 9A shows an example of editing a UI according to an embodiment.

A UI may be edited based on externally input signals according to an embodiment.

For example, UIs may be added, deleted, relocated, or resized based on user inputs. Furthermore, languages, fonts, and a UI color of the UIs may be changed based on user inputs.

For example, location or size of a button type UI may be changed based on a user input.

As shown in FIG. 9, location or size of a UI may be changed based on a predetermined input from a user with respect to the UI. The predetermined input according to an embodiment may include at least one from between one click and click for a predetermined period of time with respect to a UI. Furthermore, the predetermined input may include a plurality of inputs that are simultaneously input.

For example, an edit starting signal may be received via a click on a first button from among button type UIs for from about 1 second to about 1.5 seconds and the first button may be relocated by receiving a drag-and-drop signal 21 to a target location for the first button.

The drag-and-drop signal 21 may be a seamless user input signal. In other words, the drag-and-drop signal 21 for the first button may be a seamlessly applied signal. For example, the drag-and-drop signal 21 may be applied with a single touch. However, the embodiments are not limited thereto.

Furthermore, the size of the first button may be increased or decreased by receiving an edit starting signal and receiving a drag signal with respect to the borderlines of the first button in a predetermined signal, for example.

Furthermore, a UI may be deleted by clicking the corresponding UI again after an edit starting signal is received.

Furthermore, a UI add starting signal may be received via a user click 23 for a few seconds (e.g., from about 1 second to about 2 seconds) on an empty space other than a UI and a UI may be added.

Furthermore, the function of an existing UI or a newly added UI may be reconfigured based on an external input signal including a plurality of clicks to the corresponding UI or a predetermined pattern input (e.g., star-like pattern, triangular pattern, or rectangular pattern), for example. In other words, functions applicable to a corresponding UI (e.g., switch between a 2D image and a 3D image, resolution control, etc.) may be switched and displayed on the corresponding UI by a predetermined pattern or a click.

Furthermore, according to another embodiment, functions applicable to an existing UI or a newly added UI may be provided in the form of a pre-set table, for example.

For example, such a table may be popped up or displayed in an empty space of the control panel 2500. When functions applicable to a UI are provided, functions regarding an existing UI or a newly added UI may be reconfigured based on matching inputs of a user (e.g., sequential clicks, drag-and-drops, etc.). However, the embodiments are not limited thereto.

A sequence for matching a UI to functions may be either selecting a function to be applied based on a user input and selecting a UI for applying the selected function or selecting a UI for function reconfiguration and selecting a function to be applied to the selected UI.

Similarly, languages, fonts, and colors displayed on an existing UI or a newly added UI may be changed. In other words, letters and numbers displayed on a UI may be changed in correspondence to a language spoken by a user by receiving an externally input signal, such as a signal for selecting a nationality of the user.

Furthermore, a language displayed on a UI may be automatically changed based on the nationality included in a user profile including user identification information.

Furthermore, colors displayed on a UI may be changed by receiving an externally input signal, such as a signal for changing the colors displayed on the UI to colors selected from a pre-set color table.

FIG. 9B shows an example of using a UI changed according to an embodiment.

When a UI is changed based on motion information according to an embodiment, if a user is not fully aware of the change of the UI, the user may be confused or misuse the changed UI. Therefore, UI usage of the user with respect to the changed UI may be provided according to an embodiment, thereby preventing the user's the confusion and misuse of the UI.

The UI usage of a user may be provided in real time. Furthermore, the UI usage of a user may be provided in the form of at least one from among images including letters and numbers and sounds including voices.

For example, a UI that is used by a user for performing a predetermined function may be provided to a user via the display unit 2300 for a predetermined period of time. Therefore, the user may precisely recognize the UI to be used.

As shown in FIG. 9B, when a user presses a second button (e.g., a function for switching a 2D image to a 3D image) on a changed UI 139 (91), information 93 regarding function of the second button may be displayed on the upper-left corner of the display unit 2300. For example, when the user presses the second button (91), the information 93 indicating "2D→3D" may be displayed on the display unit 2300 for about 1 second or 1.5 seconds and disappear. However, the embodiments are not limited thereto.

Furthermore, as shown in FIG. 9B, as the user presses the second button 91, the function of the second button (e.g., a function for switching a 2D image to a 3D image) may be performed and a 3D image 115 regarding a target object may be obtained.

Furthermore, UI usage of a user may be provided in the form of sounds including voices. As described above, when the user presses the second button, UI usage of the user may be provided in the form of a voice message saying "Switching from 2D to 3D."

FIG. 10 shows an aspect that a UI is provided according to an embodiment.

A UI according to an embodiment may be displayed via at least one from between the display unit 2300 on which a captured image of a target object is displayed and the control unit 2500 including display function.

Figure 10A:
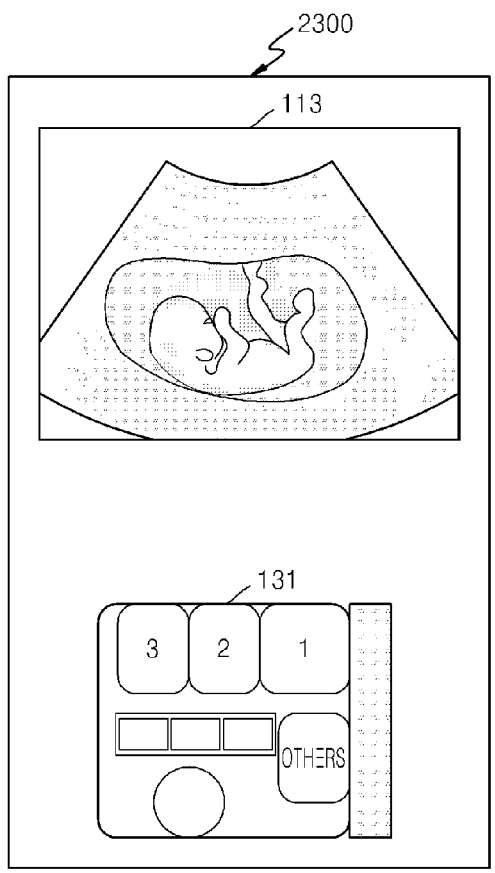
FIGS. 10A-10B show an aspect that a UI is provided according to an embodiment.

As portable medical devices are demanded and medical devices are becoming more compact, a display screen for displaying an image regarding a target object and a display screen for providing a control panel may co-exist on a single touch screen. In other words, as shown in FIG. 10A, an image 113 regarding a target object may be provided on the same screen (e.g., the display unit 2300) as the UI pattern 131.

However, such an integrated type display unit may cause difficulty of recognizing a captured image regarding a target object due to impurities including dust and a user's fingerprints.

Figure 10B:
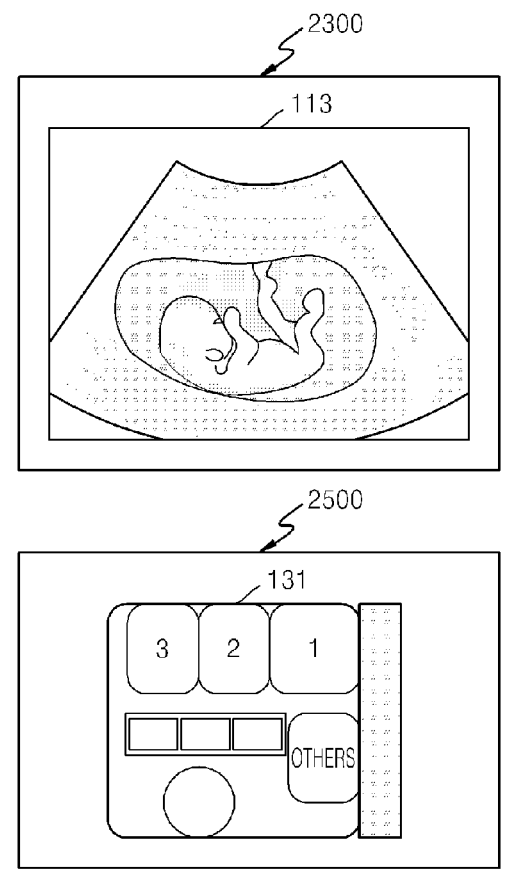

According to an embodiment, as shown in FIG. 10B, a changeable UI may be provided via the control panel 2500 having display function other than a display unit for displaying a captured image. For example, a captured image may be provided to a user via the display unit 2300, whereas the predetermined UI pattern 131 may be provided to the user independently from the captured image via the control panel 2500 having a display function.

Figure 11:
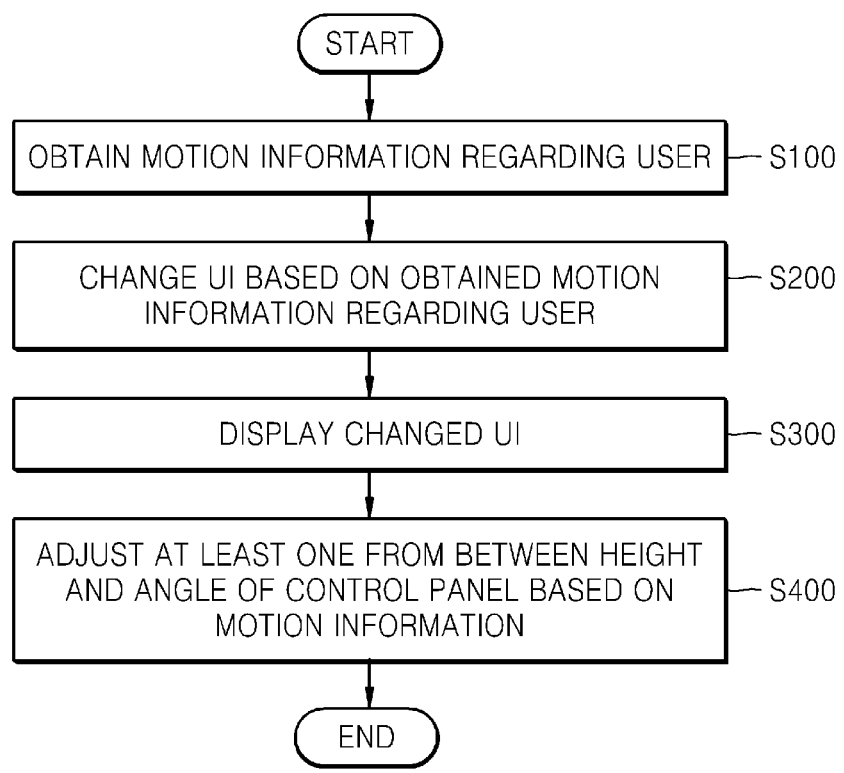
FIG. 11 is a flowchart showing a method of controlling operation of a medical device according to another embodiment.
Figure 12:
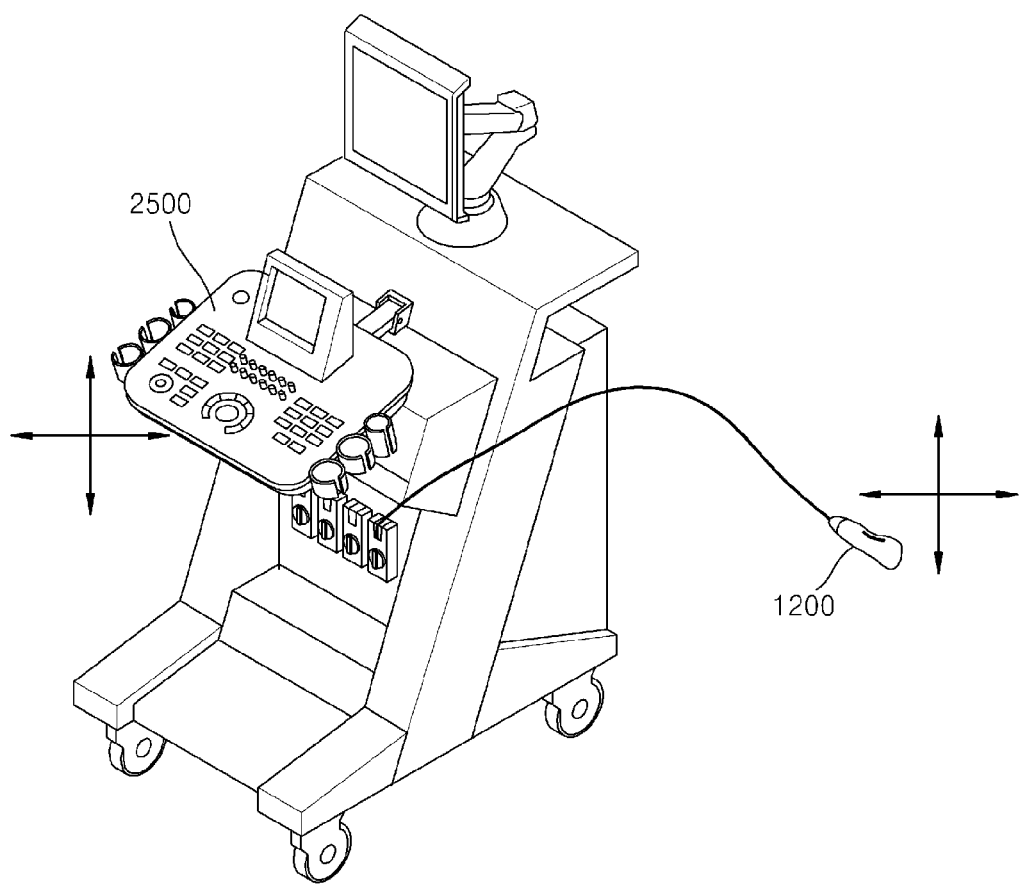
FIG. 12 shows an example of controlling operation of a medical device according to another embodiment.

FIG. 11 is a flowchart showing a method of controlling operation of a medical device according to another embodiment. FIG. 12 shows an example of controlling operation of a medical device according to another embodiment.

The method of controlling operation of a medical device according to an embodiment (see FIG. 3) may further include an operation S400 (see FIG. 4) for adjusting at least one from between height and angle of a control panel based on motion information regarding a user.

To maximize a user's convenience of operating a medical device, physical locations of predetermined components (e.g., the display unit 2300 and the control panel 2500) of a medical device may be adjusted based on motion information regarding the user which reflects postures of the user.

For example, based on by which hand a user holds a probe before a target object is imaged, locations of predetermined components (e.g., the display unit 2300 and the control panel 2500) of a medical device may be automatically adjusted.

For example, if a user holds a probe with the right hand, it is very likely the upper body of the user faces to the right as an imaging operation begins. Therefore, based on motion information obtained based on motions of the user, the display unit 2300 and the control panel 2500 may be moved upward, downward, leftward, rightward, horizontally or vertically, and at a predetermined angle. For example, the display unit 2300 and the control panel 2500 may be moved upward, downward, leftward, rightward, horizontally or vertically, and at a predetermined angle, such that the display unit 2300 and the control panel 2500 face the user (or is located in front of the user as much as possible).

Furthermore, based on motion information that may be obtained as a user imaging a target object moves, the display unit 2300 and the control panel 2500 may be moved upward, downward, leftward, rightward, horizontally or vertically, and at a predetermined angle to face the user (or is located in front of the user as much as possible), as described above.

As shown in FIG. 12, at least one from between height and angle of a control panel (a UI) may be adjusted in correspondence to movement of the probe 1200. In other words, as predetermined components (e.g., the display unit 2300, the control panel 2500, etc.) may be relocated, a user's convenience of operating a medical device may be further improved.

Figure 13:
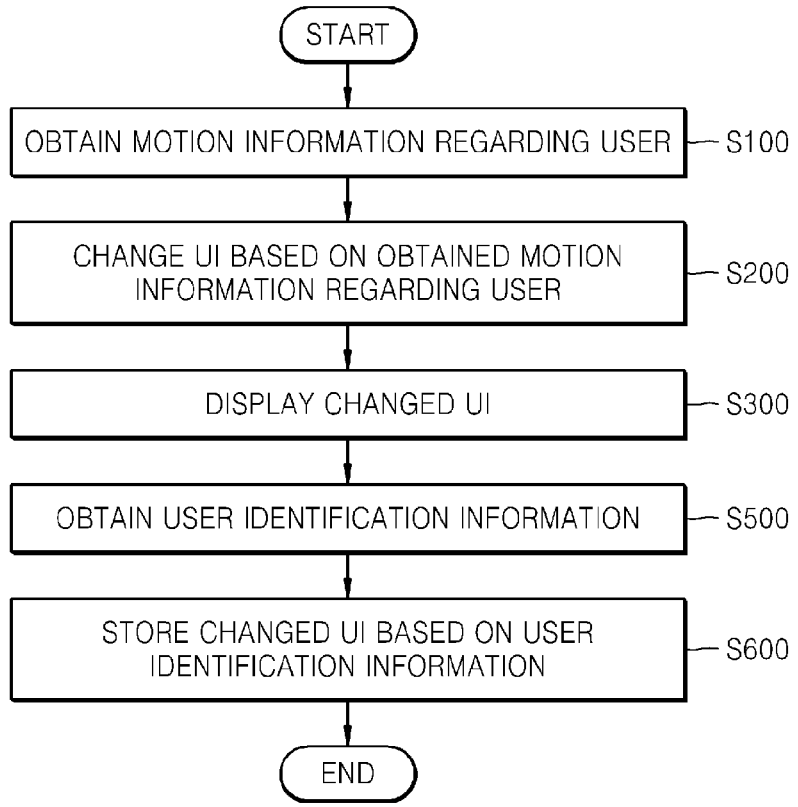
FIG. 13 is a flowchart showing a method of managing a changed UI according to another embodiment.

FIG. 13 is a flowchart showing a method of managing a changed UI according to another embodiment.

The method of managing the changed UI according to an embodiment may further include an operation S500 for obtaining user identification information and an operation S600 for storing the changed UI based on the obtained user identification information. However, the embodiments are not limited thereto. For example, the operation S500 for obtaining user identification information may be performed before the operation S100 for obtaining motion information regarding a user.

Furthermore, the operation S500 for obtaining user identification information may be performed simultaneously as the operation S100 for obtaining motion information regarding a user.

For example, simultaneously as described above, as information regarding a fingerprint of a user, information regarding an iris of the user, and information regarding a face of the user are obtained, a user profile including such biometric information regarding the user may be obtained. In other words, user identification information may be included in a user profile together with user biometric information, and such a user profile may be established in the form of a database in advance.

For example, preferred UI patterns of respective users or UIs changed according to an embodiment may be stored in correspondence to user identification information (e.g., IDs), and a user may load user stored UI pattern corresponding to user identification information of the user as occasions demand.

In other words, since physical features and behavioural features may differ from one user to another, suitable UI patterns or previously changed UI patterns are established in a database according to user identification information, and, when a user operates a medical device, a UI pattern corresponding to user identification information of the corresponding user is loaded and configures imaging conditions of the medical device. As a result, the overall imaging time may be reduced.

Figure 14:
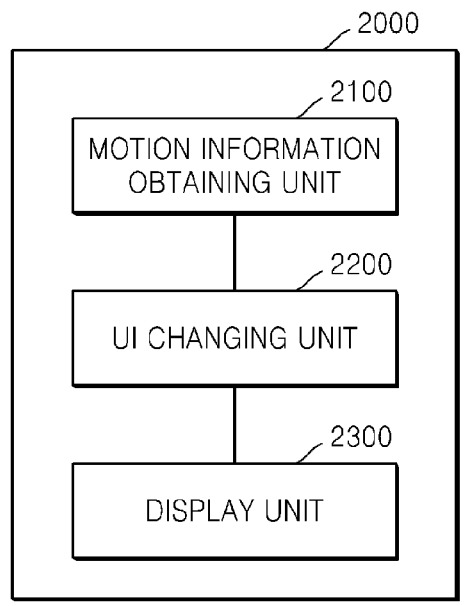
FIG. 14 shows a device for changing a UI, which is used for diagnosing a target object by using a medical device, based on motion information regarding a user and providing the changed UI, according to an embodiment.

FIG. 14 shows a device 2000 for changing a UI, which is used for diagnosing a target object by using a medical device, based on motion information regarding a user and providing the changed UI, according to an embodiment n.

The device 2000 for changing a UI, which is used for diagnosing a target object by using a medical device, based on motion information regarding a user and providing the changed UI may include a motion information obtaining unit 2100 for obtaining motion information regarding a user, a UI changing unit 2200 for changing a UI by using the obtained motion information regarding the user, and a display unit 2300 for displaying the changed UI.

The motion information obtaining unit 2100 may obtain motion information indicating whether a user uses the probe 1200 left-handedly or right-handedly.

For example, if a user is left-handed, it may be convenient for the user to locate a target object to the left and operate the probe 1200 left-handedly. Furthermore, if the user is right-handed, it may be convenient for the user to locate a target object to the right and operate the probe 1200 right-handedly. In other words, a left-handed user may perform an imaging operation by holding the probe 1200 left-handedly, whereas a right-handed user may perform an imaging operation by holding the probe 1200 right-handedly.

A user of a medical device, and more particularly, an ultrasound diagnosis device obtains an image regarding a target object by operating not only the probe 1200, but also the control panel 2500. Therefore, to increase convenience of a user of a medical device, UIs on the control panel 2500 may be arranged differently based on the user's aspect of using the probe 1200.

As described above, if a user is right-handed, it may be convenient for the user to locate a target object to the right and operate the probe 1200 right-handedly. Therefore, if button UIs and trackball UIs on the control panel 2500 are provided as a right-handed UI pattern (131 of FIG. 2B), the user may conveniently use a medical device.

Similarly, if a user is left-handed, it may be convenient for the user to locate a target object to the left and operate the probe 1200 left-handedly. Therefore, button UIs and trackball UIs on the control panel 2500 may be provided as a left-handed UI pattern (133 of FIG. 2B).

The right-handed UI pattern 131 and the left-handed UI pattern 133 on the control panel 2500 may be switched based on motion information regarding a user.

For example, if there are a user A and a user B as users of a medical device, a right-handed UI pattern (131 of FIG. 2B) may be provided on the control panel 2500 when the user A, who is right-handed, uses the medical device, whereas a left-handed UI pattern (133 of FIG. 2B) may be provided on the control panel 2500 when the user B, who is left-handed, uses the medical device.

In other words, according to an embodiment, each user may flexibly use a medical device without being restricted to its physical characteristics or motion characteristics, and user convenience may be improved by providing UIs appropriate for each user.

Change of UIs based on obtained motion information according to an embodiment may include an adaptive adjustment of imaging environment of a medical device for user to conveniently operate the medical device. As described above, a UI arrangement on the control panel 2500 may be changed based on whether a user is right-handed or left-handed, arrangements and sizes of UIs may be changed for different types of diagnosis, or arrangements and sizes of UIs may be adjusted based on frequencies of using buttons.

Figure 15:
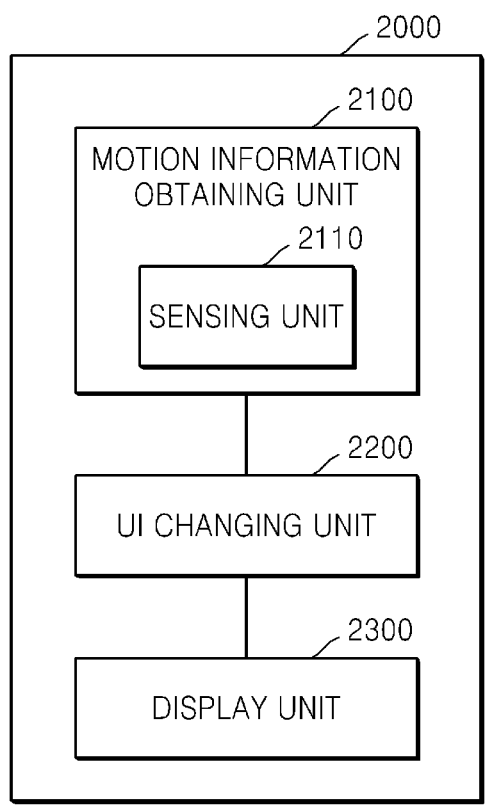
FIG. 15 is a diagram showing an apparatus further including a sensing unit according to an embodiment.

FIG. 15 is a diagram showing an apparatus further including a sensing unit 2110 according to an embodiment.

According to an embodiment, the motion information obtaining unit 2100 may further include the sensing unit 2110.

Motion information regarding a user according to an embodiment may be obtained based on information regarding current location of a probe that is obtained via the sensing unit 2110.

The information regarding current location or position of a probe according to an embodiment may include at least one from among currently pointing direction of the probe and an angle of inclination and height of the probe with respect to a predetermined reference point.

For example, the information regarding current location of a probe may be obtained based on the current pointing direction of the probe 1200. For example, information regarding the current pointing direction of the probe 1200 may be obtained via the predetermined sensor 121 that is included in the probe 1200 to be connected to an ultrasound diagnosis device (e.g., included at the tip of the probe 1200) or integrated in the ultrasound diagnosis device to which the probe 1200 is to be connected.

The predetermined sensor 121 may be configured to determine the current pointing direction of the probe 1200 based on a direction pointed by a cable connected to the probe 1200 with respect to a reference line (e.g., the center line ML of the predetermined sensor 121). In other words, the predetermined sensor 121 according to an embodiment may operate similarly as a toggle switch.

Referring back to FIG. 4A, if the probe 1200 is biased to the right from the center line ML, it may be determined that information regarding current location of the probe 1200 points to the right from an ultrasound device. In other words, information indicating that the probe 1200 is located to the right from the ultrasound device may be obtained.

On the contrary, if the probe 1200 is biased to the left from the center line ML, it may be determined that information regarding current location of the probe 1200 points to the left from an ultrasound device. In other words, information indicating that the probe 1200 is located to the left from the ultrasound device may be obtained.

Furthermore, if the probe 1200 according to an embodiment is a wireless probe, the predetermined sensor 121 may be configured to detect global positioning system (GPS) coordinates of the wireless probe 1200 via a wireless communication.

Furthermore, according to an embodiment, information regarding current location of the probe 1200 may include at least one from between an angle of inclination and a height with respect to a predetermined reference point.

As shown in FIG. 4B, the probe 1200 may include a sensor 123 for obtaining information regarding an angle of inclination or information regarding height. The sensor 123 may include a gyro sensor, a height sensor, etc.

For example, information regarding current location of the probe 1200 may be obtained as information regarding an angle of inclination with respect to a predetermined reference point. The predetermined reference point may include the ground surface on which a medical device is located, a patient table, or initial location of the probe 1200 (e.g., location of the probe 1200 when the probe 1200 is attached to an ultrasound device), for example.

Current motion of a user may be estimated in correspondence to the information regarding an angle of inclination. For example, it may be estimated that motion of the probe 1200 becomes larger as change of the angle of inclination becomes larger, and information regarding motion regarding range of angles of motion of a user operating the probe 1200 based on estimated movement of the probe 1200.

For example, the ground surface (or a patient table) and the probe 1200 may form an angle therebetween up to 90 degrees (e.g., when the probe 1200 is located perpendicular to the ground surface). A user may move the probe 1200 in a predetermined direction and at a predetermined angle during an imaging operation. The angle formed between the probe 1200 and the ground surface may be within a predetermined range (e.g., from 0 degree to 90 degrees). For example, if a user wants to obtain an ultrasound image of the liver of a patient, the probe 1200 may be moved by a user in a range between being parallel to the ground surface (e.g., the angle between the probe 1200 and the ground surface is 0 degree) and being perpendicular to the ground (e.g., the angle between the probe 1200 and the ground surface is 90 degrees).

In other words, when the probe 1200 is initially located parallel to the ground surface and the probe 1200 is then moved in a direction perpendicular to the ground surface, change of an angle of inclination may be the maximum, and movement of the probe 1200 may be estimated as the maximum. Based on the estimated movement of the probe 1200, motion information indicating that movement of a person operating the probe 1200 is also the maximum may be obtained.

Furthermore, in a similar regard, an angle of inclination at the initial location of the probe 1200 at which the probe 1200 is attached to an ultrasound device may be obtained as information regarding current location of the probe 1200.

For example, the sensor 123 according to an embodiment may indicate directions to the right or to the east from the sensor 123 as positive angles and directions to the left or the west from the sensor 123 as negative angles. However, the embodiments are is not limited thereto.

Therefore, if the probe 1200 is currently biased to the right from the initial location, a positive angle of inclination may be detected by the sensor 123, and thus information indicating that the probe 1200 is at a location corresponding to an angle of inclination detected to the right from the sensor 123. Furthermore, if the probe 1200 is currently biased to the left from the initial location, a negative angle of inclination may be detected by the sensor 123, and thus information indicating that the probe 1200 is at a location corresponding to an angle of inclination detected to the left from the sensor 123.

Furthermore, information regarding current location of the probe 1200 may be obtained as information regarding height with respect to a predetermined reference point. The predetermined reference point may include the ground surface, a patient table, or an initial location of the probe 1200 (e.g., location of the probe 1200 when the probe 1200 is attached to an ultrasound device), for example. In this case, the sensor 123 may be a height sensor.

For example, the sensor 123 may detect that the probe 1200 is located about 120 cm from the ground surface.

Furthermore, the sensor 123 may detect that the probe 1200 is located about 5 cm lower than the height corresponding to the initial state in which the probe 1200 is attached to an ultrasound device. In other words, information regarding heights with respect to predetermined reference points may be obtained as information regarding current location of the probe 1200.

Motion information indicating change of height of posture of a user operating the probe 1200 may be obtained based on information regarding height of the probe 1200 (e.g., change of height) according to an embodiment.

Motion Information regarding a user according to the present embodiment may be obtained based on biometric information regarding the user including at least one from among information regarding a fingerprint of the user, information regarding an iris of the user, and information regarding a face of the user.

Referring back to FIG. 5, based on fingerprint information 11 regarding a user obtained via a sensor 125 embedded in the probe 1200, it may be determined whether the user is currently grabbing the probe 1200 with the left hand or the right hand.

In other words, motion information indicating whether the user is using the probe 1200 with the left hand or the right hand may be obtained based on the fingerprint information 11 obtained via the sensor 125 embedded in the probe 1200.

For example, if the fingerprint information 11 corresponds to the fingerprint of the right thumb or right forefinger of a user, it is determined that the user is currently grabbing the probe 1200 with the right hand, and thus motion information indicating that the user is using the probe 1200 with the right hand may be obtained.

Furthermore, if the fingerprint information 11 corresponds to the fingerprint of the left thumb or left forefinger of a user, it is determined that the user is currently grabbing the probe 1200 with the left hand, and thus motion information indicating that the user is using the probe 1200 with the left hand may be obtained.

Furthermore, according to an embodiment, it may be determined who a user currently using the probe 1200 is based on the fingerprint information 11 obtained via the sensor 125 embedded in the probe 1200. In this case, the fingerprint information 11 may be utilized as user identification information (e.g., an ID).

Furthermore, information regarding motion of a user according to an embodiment may be obtained based on at least one from between iris information 13 and face information 15 of a user.

Referring back to FIG. 5, at least one from between the iris information 13 and the face information 15 may be obtained via a sensor 111 arranged on an ultrasound device. The sensor 111 may be arranged nearby a display unit 2300 of an ultrasound device. However, the embodiments are not limited thereto.

Furthermore, the sensor 111 may either perform both iris recognition and face recognition simultaneously or be embodied as independent sensors for iris recognition and face recognition.

According to an embodiment, the iris information 13 regarding a user may be obtained via the sensor 111 according to an embodiment. The iris information 13 may include user identification information indicating who a current user is and information regarding current locations of irises of the current user. For example, by recognizing irises of a current user via the sensor 111, information regarding identification of the current user may be obtained.

Furthermore, current line of sight of a user may be determined based on information regarding current locations of irises obtained via the sensor 111, and motion information regarding the user may be obtained based on the current line of sight of the user. In other words, information regarding current posture of the user may be obtained based on whether irises are more biased to the left or to the right. However, the embodiments are not limited thereto.

For example, if irises are substantially biased to the left in eyes of a user, it may be determined that the upper body of the user faces to the right. In other words, it may be determined that the user is operating the probe 1200 with the right hand.

Similarly, if irises are substantially biased to the right in eyes of a user, it may be determined that the upper body of the user faces to the left. In other words, it may be determined that the user is operating the probe 1200 with the left hand.

According to an embodiment, the face information 15 of a user may be obtained via the sensor 111. The face information 15 may include user identification information indicating who the user is and information regarding a direction the face the user faces. For example, information regarding who the user is may be obtained by recognizing face feature points and face silhouette of the user via the sensor 111.

Furthermore, main face of the user may be determined by using the information regarding a direction the face of the user faces obtained via the sensor 111, and motion information regarding the user may be obtained based on the main face of the user. In other words, current main face of the user may be determined based on an area of a face of the user, and information regarding current posture of the user may be obtained from the determined main face.

For example, when an area of the right face of a user is compared to the area of the left face of the user and it is determined that the left face of the user is larger than the right face of the user, it may be determined that the upper body of the user faces to the right. In other words, it may be determined that the user is operating the probe 1200 with the right hand.

Similarly, when the area of right face of a user is compared to the area of the left face of the user and it is determined that the right face of the user is larger than the right face of the user, it may be determined that the upper body of the user faces to the left. In other words, it may be determined that the user is operating the probe 1200 with the left hand.

Furthermore, motion information regarding a user may be obtained by using the iris information 13 and the face information 15 of the user. For example, when the area of the right face of a user is compared to the area of the left face of the user and it is unclear which of the left face and the right face is larger than the other, information regarding irises of the user may be further utilized as described above for obtaining the motion information regarding the user.

A UI according to an embodiment may include at least one from among a shortkey, a switch, a keyboard, and a trackball that indicate functions to be used for diagnosis of a target object.

Referring back to FIG. 6, a UI for displaying operation functions to be used during a diagnosis of a target object according to an embodiment may include a keyboard 611, buttons or switches 613, and trackballs 615.

A UI according to an embodiment may include a keyboard type UI 611 for inputting letters and numbers in relation to imaging of a target object, at least one button or switch type UI 613 and trackball type UI 615 indicating predetermined functions, such as image zoom in/out, resolution control, switch between a 2D image and a 3D image, etc.

At least one from among the keyboard type UI 611, the button or switch type UI 613, and the trackball type UI 615 may be provided as a virtual UI layout.

In other words, a UI according to an embodiment is not necessarily in the physical form and may be virtually embodied to indicate a predetermined function in the form of letters, numbers, and images on the display unit 2300 or the control panel 2500.

The UI changing unit 2200 according to an embodiment may change at least one from among shape, size, and location of a UI based on obtained motion information regarding a user.

Referring back to FIG. 7A, the shape of a UI may be changed based on the motion information regarding the user.

For example, if the moving range of the probe 1200 significantly increases (that is, if motion of a user significantly increases), it may be inconvenient for the user to touch the UI 611 through 615. In other words, a hand of the user may not reach the UI or it may be difficult for the user to operate the UI.

In this case, according to an embodiment, the shape of the UI may be changed for improving user convenience. For example, shape a UI (1 through 3 of 131), which is simplification of the keyboard type UI 611 or the button or switch type UI 613 of FIG. 6, may be changed and the changed UI 132 may be provided. For example, if the user uses a button 2 more frequently than buttons 1 and 3 during an imaging operation, shape of the button 2 may be changed to a triangle in which the base is longer than the other sides, such that the user may access the button 2 more easily. In other words, a change may be made, such that the button 2 is larger than the button 1 or the button 3.

Furthermore, according to an embodiment, locations of the buttons 1 through 3 may be changed. For example, the UI may be changed, such that the buttons 1 through 3 are arranged in the order of the button 3, the button 1, and the button 2. In this case, the button 1 may be the most frequently used button and may have a triangular shape in which the base is longer than the other sides. However, the embodiments are not limited thereto.

Furthermore, referring back to FIG. 7B, size of a UI may be changed based on motion information regarding a user.

As described above, when motion of a user increases, a changed UI 135 in which sizes of buttons of the UI pattern 131 may be overall or partially increased and decreased may be provided, such that the user may easily access the buttons.

For example, sizes of the buttons 1 through 3 may be increased for easier access of a user. Similarly, locations of the buttons 1 through 3 may be changed to be closer to the user for easier access of the user.

Referring back to FIG. 7C, different UI patterns may be provided based on physical features of a user.

For example, if the user is right-handed, the right-handed UI pattern 131 may be provided. Furthermore, if the user is left-handed, the left-handed UI pattern 133 may be provided. The right-handed UI pattern 131 and the left-handed UI pattern 133 may be symmetrical to each other and may be switched based on motion information regarding the user as described above.

At least one from among shape, size, and location of a UI may be changed based on frequencies of accessing functions that are used during a diagnosis of a target object, according to an embodiment.

Referring back to FIG. 8, as shown in FIGS. 8B and 8C, at least one from among shape, size, and location of the UI pattern 131 of FIG. 7 may be changed (a UI pattern 137 or a UI pattern 139) based on frequencies of accessing functions that are used during a diagnosis of a target object. For convenience of explanation, it is assumed that the UI pattern 131 is the basic pattern that may be provide by a medical device.

For example, for a predetermined diagnosis item, a trackball may not be used, and a function corresponding to a second button from among button type UIs indicated as first through third buttons may be used more frequently than the others. In this case, as shown in FIG. 8B, a circular UI corresponding to a trackball function may be omitted, and a UI corresponding to the second button may be changed to have the largest size.

In other words, UIs that are not used or less frequently by a user may be omitted and size of a frequently used UI may be increased, thereby improving UI accessibility and convenience of a user operating a medical device.

For another example, if a user frequently uses a trackball and a third button (e.g., zoom in/out function) from among button type UIs for a predetermined diagnosis item, sizes of the circular UI corresponding to a trackball and the third button from among the button type UIs in the basic pattern 131 may be increased (the UI pattern 139), as shown in FIG. 8C.

Furthermore, UIs may be arranged in a radial shape in correspondence to fingers of a user as shown in the pattern 139 as shown in FIG. 8C. However, the embodiments are not limited thereto.

Furthermore, frequencies of using functions may differ based on types of diagnosis, different UI patterns may be provided in correspondence to different types of diagnosis.

For example, frequencies of using functions provided by an ultrasound device may differ based on types of diagnosis including heart ultrasound diagnosis, liver ultrasound diagnosis, abdominal ultrasound diagnosis, Pelvic ultrasonography, Doppler ultrasound diagnosis, etc. For example, image zoom in/out function and trackball function may be frequently used for a heart ultrasound diagnosis, whereas resolution controlling function may be more frequently used than the image zoom in/out function and the trackball function for a liver ultrasound diagnosis.

In other words, for heart ultrasound diagnosis, sizes of a UI for performing image zoom in/out function and a UI for performing trackball function may be larger than other UIs and may be arranged at the center of the control panel 2500, for example.

On the contrary, for liver ultrasound diagnosis, sizes of a UI for performing image zoom in/out function and a UI for performing trackball function may be reduced or the UI for performing image zoom in/out function and the UI for performing trackball function may be omitted, whereas a UI for performing a resolution controlling function may be larger than other UIs and may be arranged at the center of the control panel 2500.

Figure 16:
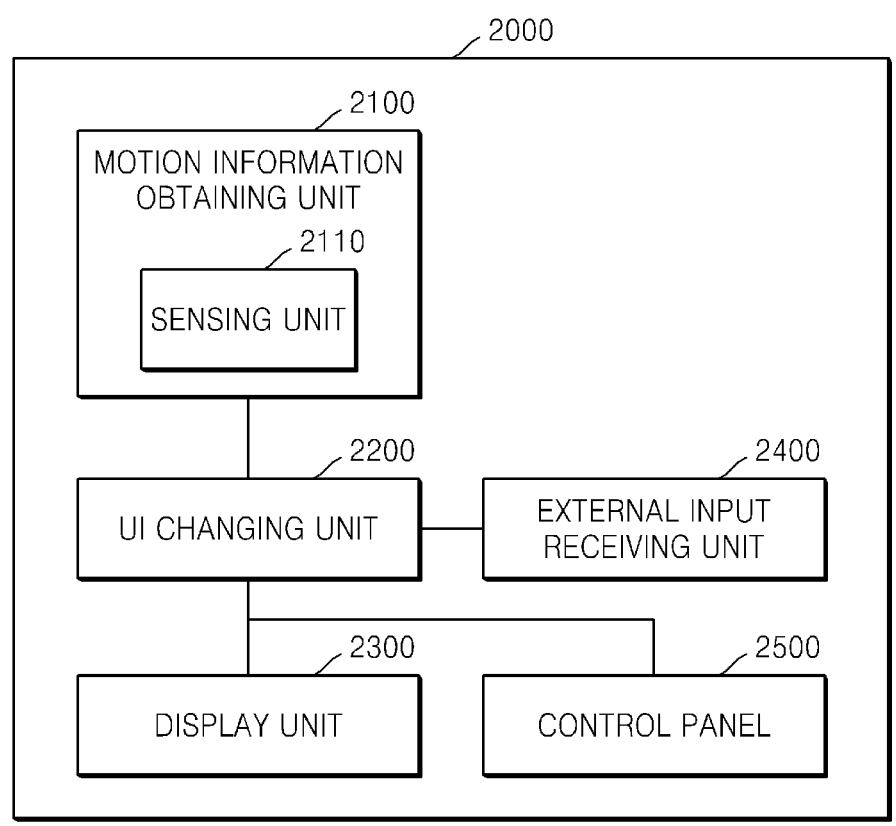
FIG. 16 is a diagram showing an apparatus further including a sensing unit, an external input receiving unit, and a control panel.

FIG. 16 is a diagram showing an apparatus 2000 further including a sensing unit, an external input receiving unit 2400, and a control panel.

The apparatus 2000 according to an embodiment may further include the external input receiving unit 2400.

A UI according to an embodiment may be changed by the UI changing unit 2200 based on externally input signals received via the external input receiving unit 2400.

UIs according to an embodiment may be added, deleted, relocated, or resized based on user inputs. Furthermore, languages, fonts, and UI colors of UIs may be changed based on user inputs.

For example, locations or sizes of button type UIs may be changed based on user inputs.

Referring back to FIG. 9, location or size of a UI may be changed based on a predetermined input from a user with respect to the UI. The predetermined input according to an embodiment may include at least one from among one click and click for a predetermined period of time with respect to a UI. Furthermore, the predetermined input may include a plurality of inputs that are simultaneously input.

For example, an edit starting signal may be received via a click on a first button from among button type UIs for from about 1 second to about 1.5 seconds, and the first button may be relocated by receiving a drag-and-drop signal 21 to a target location for the first button.

The drag-and-drop signal 21 may be a seamless user input signal. In other words, the drag-and-drop signal 21 to the first button may be a seamlessly applied signal. For example, the drag-and-drop signal 21 may be applied with a single touch. However, the embodiments are not limited thereto.

Furthermore, the size of the first button may be increased or decreased by receiving an edit starting signal and receiving a drag signal with respect to the borderlines of the first button in a predetermined signal, for example.

Furthermore, a UI may be deleted by clicking the corresponding UI again after an edit starting signal is received.

Furthermore, a UI add starting signal may be received via a user click 23 for a few seconds (e.g., from about 1 second to about 2 seconds) on an empty space other than a UI and a UI may be added.

Furthermore, the function of an existing UI or a newly added UI may be reconfigured based on an external input signal including a plurality of clicks to the corresponding UI or a predetermined pattern input (e.g., star-like pattern, triangular pattern, or rectangular pattern), for example. In other words, functions applicable to a corresponding UI (e.g., switch between a 2D image and a 3D image, resolution control, etc.) may be switched and displayed on the corresponding UI by a predetermined pattern or a click.

Furthermore, according to another embodiment, functions applicable to an existing UI or a newly added UI may be provided in the form of a pre-set table, for example.

For example, such a table may be popped up or displayed in an empty space of the control panel 2500. When functions applicable to a UI are provided, functions regarding an existing UI or a newly added UI may be reconfigured based on matching inputs of a user (e.g., sequential clicks, drag-and-drops, etc.). However, the embodiments are not limited thereto. A sequence for matching a UI to functions may be either selecting a function to be applied based on a user input and selecting a UI for applying the selected function or selecting a UI for function reconfiguration and selecting a function to be applied to the selected UI.

Similarly, languages, fonts, and colors displayed on an existing UI or a newly added UI may be changed. In other words, letters and numbers displayed on a UI may be changed in correspondence to a language spoken by a user by receiving an externally input signal, such as a signal for selecting the nationality of the user. Furthermore, a language displayed on a UI may be automatically changed based on the nationality included in a user profile including user identification information.

Furthermore, colors displayed on a UI may be changed by receiving an externally input signal, such as a signal for changing the colors displayed on the UI to colors selected from a pre-set color table.

The apparatus 2000 according to an embodiment may further include the control panel 2500 including a display function.

A UI according to an embodiment may be displayed via at least one from among the display unit 2300 and the control panel 2500.

A UI according to an embodiment may be displayed via at least one from among the display unit 2300 on which a captured image regarding a target object is displayed and the control panel 2500 including display function.

As portable medical devices are demanded and medical devices are becoming more compact, a display screen for displaying an image regarding a target object and a display screen for providing a control panel may co-exist on a single touch screen. In other words, as shown in FIG. 10A, an image 113 regarding a target object may be provided on the same screen (e.g., the display unit 2300) as the UI pattern 131.

However, such an integrated type display unit may cause difficulty of recognizing a captured image regarding a target object due to impurities including dusts and a user's fingerprints.

Referring back to FIG. 10B, a changeable UI may be provided via the control panel 2500 having display function other than a display unit for displaying a captured image. For example, a captured image may be provided to a user via the display unit 2300, whereas the predetermined UI pattern 131 may be provided to the user independently from the captured image via the control panel 2500 having display function.

Figure 17:
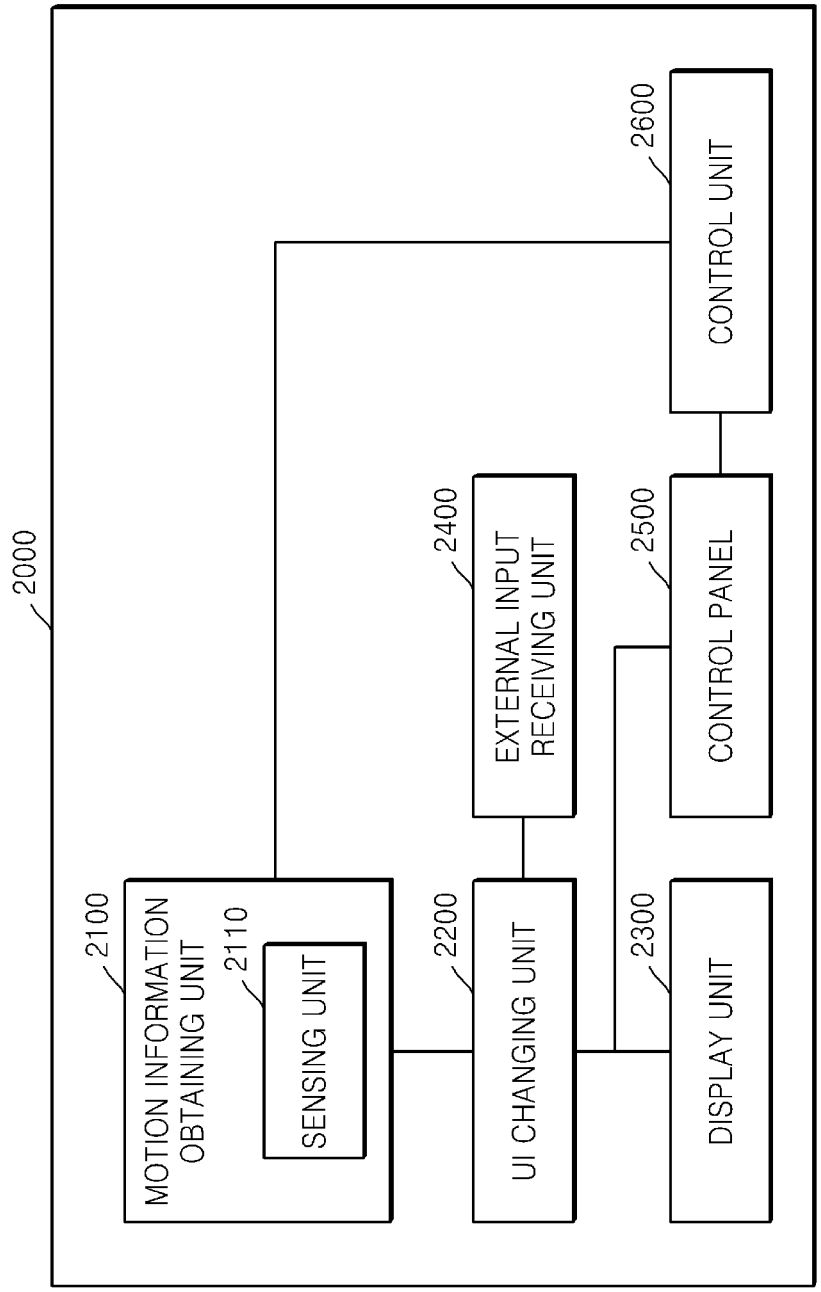
FIG. 17 is a diagram showing an apparatus including a sensing unit, an external input receiving unit, a control panel, and a control unit.

FIG. 17 is a diagram showing an apparatus 2000 including a sensing unit, an external input receiving unit, a control panel, and a control unit.

The apparatus 2000 may further include a control unit 2600. The control unit 2600 may adjust at least one from between height and angle of the control panel 2500 based on motion information regarding a user.

To maximize a user's convenience of operating a medical device, physical locations of predetermined components (e.g., the display unit 2300 and the control panel 2500) of a medical device may be adjusted based on motion information regarding the user which reflects postures of the user.

For example, based on by which hand a user holds a probe before a target object is imaged, locations of predetermined components (e.g., the display unit 2300 and the control panel 2500) of a medical device may be automatically adjusted.

For example, if a user holds a probe with the right hand, it is very likely the upper body of the user to face to the right as an imaging operation begins. Therefore, based on motion information obtained based on motions of the user, the display unit 2300 and the control panel 2500 may be moved upward, downward, leftward, rightward, horizontally or vertically, and at a predetermined angle. For example, the display unit 2300 and the control panel 2500 may be moved upward, downward, leftward, rightward, horizontally or vertically, and at a predetermined angle, such that the display unit 2300 and the control panel 2500 face the user (or is located in front of the user as much as possible).

Furthermore, based on motion information that may be obtained as a user imaging a target object moves, the display unit 2300 and the control panel 2500 may be moved upward, downward, leftward, rightward, horizontally or vertically, and at a predetermined angle to face the user (or is located in front of the user as much as possible), as described above. Referring back to FIG. 12, at least one from among height and angle of a control panel may be adjusted in correspondence to movement of the probe 1200. In other words, as predetermined components (e.g., the display unit 2300, the control panel 2500, etc.) may be relocated, a user's convenience of operating a medical device may be further improved.

Figure 18:
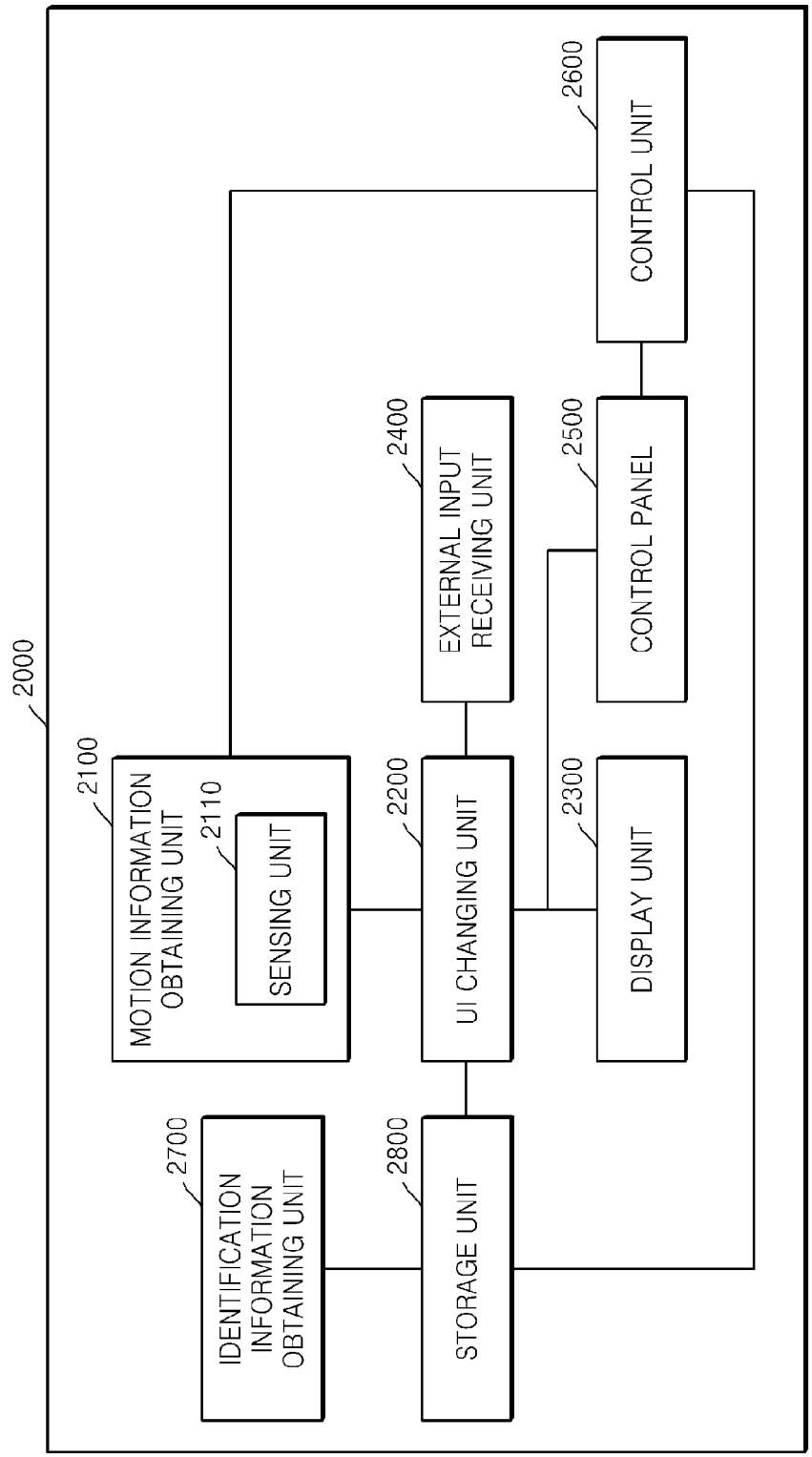
FIG. 18 is a diagram showing an apparatus for changing a UI based on motion information regarding a user and providing the changed UI according to another embodiment.

FIG. 18 is a diagram showing an apparatus 2000 for changing a UI based on motion information regarding a user and providing the changed UI according to another embodiment.

The apparatus 2000 may include the motion information obtaining unit 2100, the UI changing unit 2200, the display unit 2300, the external input receiving unit 2400, the control panel 2500, and the control unit 2600, and may further include a identification information obtaining unit 2700 for obtaining user identification information and a storage unit 2800 for storing the changed UI based on the user identification information.

The identification information obtaining unit 2700 may obtain user identification information. The user identification information may be stored in the storage unit 2800 together with a changed UI. However, the embodiments are not limited thereto.

According to an embodiment, user identification information may be obtained before motion information regarding a user is obtained.

Furthermore, user identification information may be obtained simultaneously as motion information regarding a user is obtained. For example, simultaneously as described above, as information regarding fingerprint of a user, information regarding iris of the user, and information regarding face of the user are obtained, user profile including such biometric information regarding the user may be obtained. In other words, user identification information may be included in a user profile together with user biometric information, and such a user profile may be established in the form of a database in advance.

For example, preferred UI patterns of respective users or UIs changed according to an embodiment may be stored in correspondence to user identification information (e.g., IDs), and a user may load a user stored UI pattern corresponding to user identification information of the user as occasions demand.

In other words, since physical features and behavioural features may differ from one user to another, suitable UI patterns or previously changed UI patterns are established in a database according to user identification information, and, when a user operates a medical device, a UI pattern corresponding to user identification information of the corresponding user is loaded and configures imaging conditions of the medical device. As a result, the overall imaging time may be reduced.

The above-described method may be applied to the apparatus according to embodiments. Thus, a description of the apparatus that is similar to the description of the method will not be repeated here.

The above-described embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs or DVDs).

The embodiments have been described by referring to exemplary embodiments. While the exemplary embodiments have been particularly shown and described, it will be understood by those of ordinary skill in the art that various changes in form and details may be made therein without departing from the spirit and scope of the embodiments as defined by the appended claims. Therefore, the exemplary embodiments should be considered in a descriptive sense only and not for purposes of limitation. Therefore, the scope of the embodiments is defined not by the detailed description of the exemplary embodiments, but by the appended claims, and all differences within the scope will be construed as being included in the embodiments.

What is claimed is:

1. A method comprising:
    displaying a graphical user interface (GUI) on a screen, the displayed GUI including a plurality of user interfaces to control a medical device used for diagnosis of a target object, each user interface of the plurality of user interfaces having a shape, size and location displayed on the screen;
    obtaining user motion information regarding a user of the medical device; and
    for at least one user interface of the plurality of user interfaces, changing at least one of the shape, the size and the location of the at least one user interface displayed on the screen to a different shape, size and location, respectively, displayed on the screen, based on the obtained user motion information regarding the user, to thereby display a changed GUI having an improved ease of access to the at least one user interface, as compared to the GUI before being changed, by the user for a current position of the user at which the user uses the medical device.

2. The method of claim 1, wherein the user motion information regarding the user is obtained based on position information regarding a current position of a probe of the medical device.

3. The method of claim 2, wherein the position information regarding the current position of the probe comprises at least one from among a current pointing direction of the probe and an angle of inclination and a height of the probe with respect to a predetermined reference point.

4. The method of claim 1, wherein the user motion information regarding the user is obtained based on biometric information regarding the user including at least one from among information regarding a fingerprint of the user, information regarding an iris of the user, and information regarding a face of the user.

5. The method of claim 1, wherein the at least one user interface comprises at least one from among a shortkey, a switch, a keyboard, and a trackball that indicate functions to be used for diagnosis of the target object.

6. The method of claim 1, wherein, the at least one of the shape, the size and the location is the location.

7. The method of claim 5, wherein the changing changes the at least one of the shape, the size, and the location based on frequency of accessing functions that are used during a diagnosis of the target object.

8. The method of claim 5, further comprising:
editing the GUI based on externally input signals.

9. The method of claim 1, wherein the screen is a screen of a control panel of the medical device on which a captured image is displayed.

10. The method of claim 9, further comprising:
adjusting at least one of a height and an angle of the control panel based on the user motion information regarding the user.

11. The method of claim 1, further comprising:
obtaining user identification information regarding the user; and
storing the changed GUI based on obtained user identification information.

12. A non-transitory computer readable recording medium having recorded thereon a computer program for implementing the method of claim 1.

13. An apparatus comprising:
at least one memory storing instructions; and
at least one processor that executes the instructions to cause the following to be performed:
displaying a graphical user interface (GUI) on a screen, the displayed GUI including a plurality of user interfaces to control a medical device used for diagnosis of a target object, each user interface of the plurality of user interfaces having a shape, size and location displayed on the screen,
obtaining user motion information regarding a user of the medical device, and
for at least one user interface of the plurality of user interfaces, changing at least one of the shape, the size and the location of the at least one user interface displayed on the screen to a different shape, size and location, respectively, displayed on the screen, based on the obtained user motion information regarding the user, to thereby display a changed GUI having an improved ease of access to the at least one user interlace, as compared to the GUI before being changed, by the user for a current position of the user at which the user uses the medical device.

14. The apparatus of claim 13, further comprising:
a sensor to sense a current position of a probe of the medical device,
wherein the obtaining obtains the user motion information regarding the user based on information regarding the current position of the probe sensed by the sensor.

15. The apparatus of claim 14, wherein the information regarding the current position of the probe comprises at least one from among a current pointing direction of the probe and an angle of inclination and a height of the probe with respect to a predetermined reference point.

16. The apparatus of claim 13, wherein the obtaining obtains the user motion information regarding the user based on biometric information regarding the user including at least one from among information regarding a fingerprint of the user, information regarding an iris of the user, and information regarding a face of the user.

17. The apparatus of claim 13, wherein the at least one user interlace comprises at least one from among a shortkey, a switch, a keyboard, and a trackball that indicate functions to be used for diagnosis of the target object.

18. The apparatus of claim 13, wherein, the at least one of the shape, the size and the location is the location.

19. The apparatus of claim 17, wherein the changing changes the at least one of the shape, the size, and the location based on frequency of accessing functions used during a diagnosis of the target object.

20. The apparatus of claim 17, wherein the at least one processor executes the instructions to further cause the following to be performed:
receiving an external input signal, and
editing the GUI based on the received externally input signal.

21. The apparatus of claim 13, wherein the changed GUI is displayed on a control panel of the medical device and on which a captured image is displayed.

22. The apparatus of claim 13, wherein the at least one processor executes the instructions to further cause the following to be performed:
adjusting at least one of a height and an angle of a control panel of the medical device based on the user motion information regarding the user.

23. The apparatus of claim 13, wherein the at least one processor executes the instructions to further cause the following to be performed:
obtaining user identification information regarding the user, and
storing the changed GUI based on the user identification information.

24. A method, comprising:
determining, based on detected motion of a user of a medical device when the user is using the medical device, a use pattern of the user; and
changing, based on the determined use pattern, displayed locations of user interfaces for controlling the medical device and included in a graphical user interface (GUI) displayed on a screen, to thereby optimize a layout of the user interfaces in the GUI,
to thereby display a changed GUI having an improved ease of access to the user interfaces, as compared to the GUI before being changed, by the user based on the determined use pattern.

25. The method of claim 24, wherein the layout is stored responsive to an identity of the user.

26. The method of claim 24, wherein determining the use pattern determines the use pattern based on at least one of detected handedness of the user, detected finger position of the user, detected iris position of the user, detected face position of the user, detected probe motion of a probe of the medical device, and detected frequency of function access of the user.

* * * * *

UNITED STATES PATENT AND TRADEMARK OFFICE
CERTIFICATE OF CORRECTION

PATENT NO. : 9,904,455 B2  
APPLICATION NO. : 14/320924  
DATED : February 27, 2018  
INVENTOR(S) : Dae-hyun Ban et al.

Page 1 of 1

It is certified that error appears in the above-identified patent and that said Letters Patent is hereby corrected as shown below:

In the Claims

Column 29, Line 65:  
In Claim 13, delete "interlace," and insert -- interface, --, therefore.

Column 30, Line 19:  
In Claim 17, delete "interlace" and insert -- interface --, therefore.

Signed and Sealed this  
Twenty-ninth Day of May, 2018

Andrei Iancu  
*Director of the United States Patent and Trademark Office*